(12) United States Patent
Kurnik et al.

(10) Patent No.: US 7,668,663 B2
(45) Date of Patent: Feb. 23, 2010

(54) LEVENBERG-MARQUARDT OUTLIER SPIKE REMOVAL METHOD

(75) Inventors: Ronald T. Kurnik, Foster City, CA (US); Laurent Francioli, Lutry (CH); Rolf Knobel, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 456 days.

(21) Appl. No.: 11/316,315

(22) Filed: Dec. 20, 2005

(65) Prior Publication Data

US 2007/0148632 A1    Jun. 28, 2007

(51) Int. Cl.
G01N 33/48        (2006.01)
(52) U.S. Cl. .......................................... 702/19
(58) Field of Classification Search .................... 702/19
See application file for complete search history.

(56) References Cited

U.S. PATENT DOCUMENTS

| 2007/0143070 A1 | 6/2007 | Kurnik et al. |
| 2007/0143385 A1 | 6/2007 | Kurnik et al. |
| 2008/0033701 A1 | 2/2008 | Kurnik |

FOREIGN PATENT DOCUMENTS

| WO | WO 97/46707 A2 | 12/1997 |
| WO | WO 97/46707 A3 | 12/1997 |
| WO | WO 97/46712 A2 | 12/1997 |
| WO | WO 97/46712 A3 | 12/1997 |
| WO | WO 97/46714 A1 | 12/1997 |

OTHER PUBLICATIONS

Kurnik, R.T. et al., "Application of the Mixtures of Experts Algorithm for Signal Processing in a Noninvasive Glucose Monitoring System," *Sensors and Actuators B*, 1999, vol. 60, pp. 19-26.
Lourakis, M.I.A., "A Brief Descritption of the Levenberg-Marquardt Algorithm Implemened by levmar," Feb. 11, 2005, pp. 1-6.
McLauchlan, P., "Robust Observations," located at <http://gandalf-library.sourceforge.net/tutorial/report/node131.html>, Mar. 17, 2006, last visited on Jan. 25, 2008, two pages.
Motulsky, H. et al., *Fitting Models to Biological Data Using Linear and Nonlinear Regression, Version 4.0*, GraphPad Software, Inc., 2003, pp. 3-11 (Table of Contents Only).
Motulsky, H., *Statistics Guide Statistical Analyses for Laboratory and Clinical Researchers, Version 4.0*, GraphPad Software, Inc., Feb. 2005, six pages (Table of Contents Only).
Wang, S-S. et al., "Homogeneous Real-Time Detection of Single-Nucleotide Polymorphisms by Strand Displacement Amplification on the BD ProbeTec ET System," *Clinical Chemistry*, 2003, vol. 49, No. 10, pp. 1599-1607.
Weisstein, E., "Cubic Spline," located at <http://mathwolrd.wolfram.com/CubicSpline.html>, 1999, last visited on Jan. 25, 2008, four pages.
Weusten, J.J.A.M. et al., "Principles of Quantitation of Viral Loads Using Nucleic Acid Sequence-Based Amplification in Combination With Homogeneous Detection Using Molecular Beacons," *Nucleic Acids Research*, 2002, vol. 30, No. 6, e26, seven pages.
Bieche, I. et al, "Quantitation of *MYC* Gene Expression in Sporadic Breast Tumors With a Real-Time Reverse Transcription-PCR assay," *Cancer Research*, Jun. 15, 1999, vol. 59, pp. 2759-2765.
Cambridge University Press, "Root Finding and Nonlinear Sets of Equations," Chapter 9 in *Numerical Recipes In C: The Art of scientific Computing*, 1988-1992, pp. 347-369.
Gibson, U.E.M. et al., "A Novel Method for Real Time Quantitative RT-PCR," *Genome Research*, 1996, vol. 6, pp. 995-1001.

*Primary Examiner*—Jerry Lin
(74) *Attorney, Agent, or Firm*—Townsend and Townsend and Crew LLP; Gerald T. Gray

(57) ABSTRACT

Systems and methods for identifying and removing spikes in data sets representing PCR growth curves or other sigmoid type curves or growth curves. A double sigmoid function with parameters determined using a Levenberg-Marquardt regression algorithm is used to find an approximation to the curve, and a statistical test such as a z-test is then used to identify spikes by identifying data points in the data set that do not fit well with the approximation. The identified spike(s) are removed from the data set and/or replaced with interpolated data points determined by using data points surrounding the identified spike(s). In one aspect, a spline interpolation process such as a cubic spline interpolation process is used to find an approximation to the data set with the identified spike points removed. Interpolated values to replace the spike points are then calculated using the cubic spline interpolation approximation curve.

21 Claims, 25 Drawing Sheets

Figure 2: Levenberg-Marquardt robust approximation
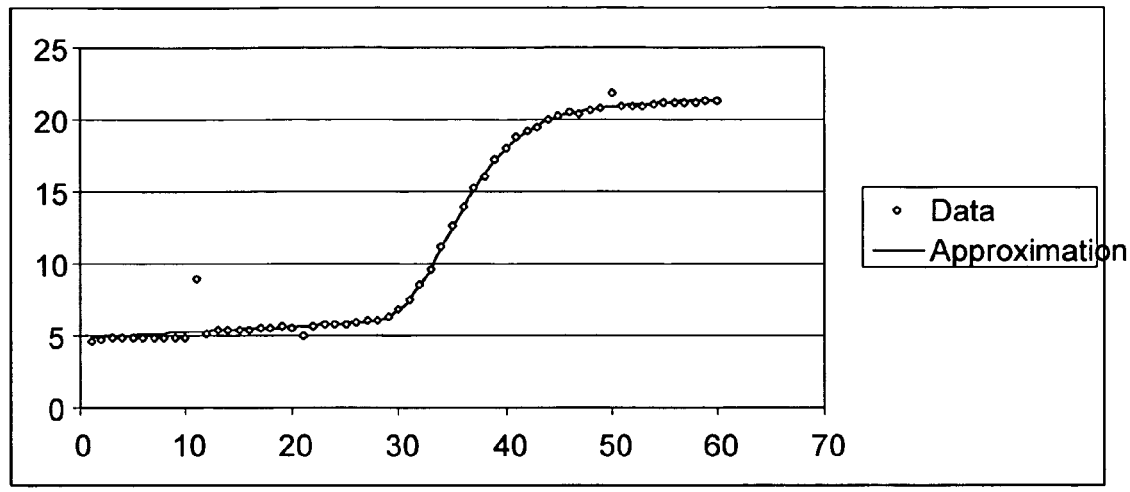
Figure 3: Detect outliers using a Z-Test
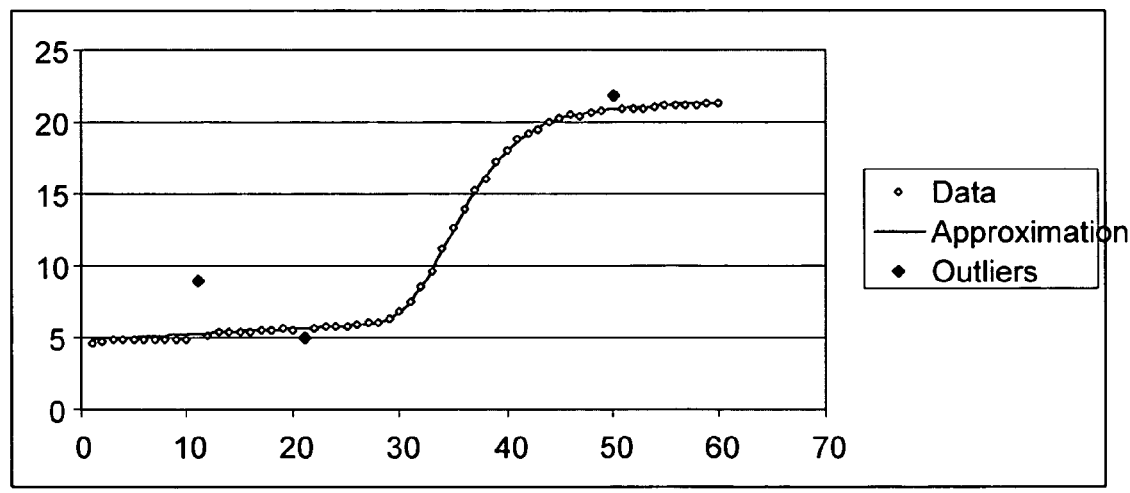

Figure 4: Replace outliers using a cubic spline interpolation
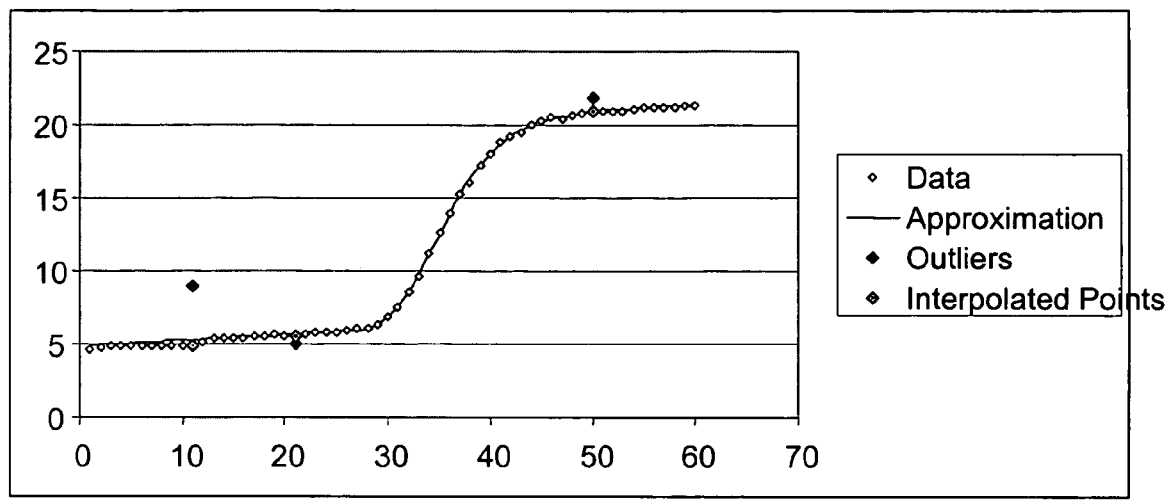
Figure 6: Double sigmoid decomposition
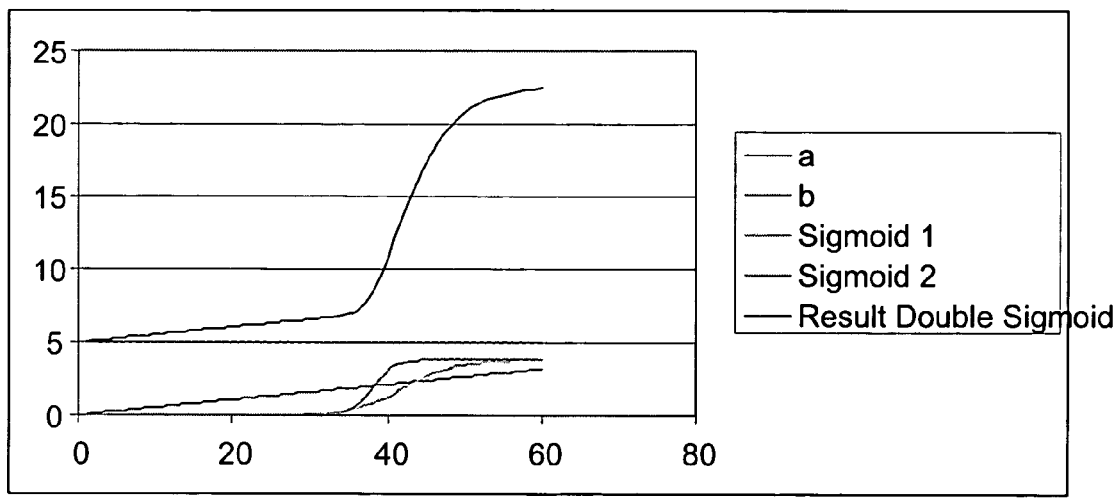

Figure 7: The parameters of a sigmoid
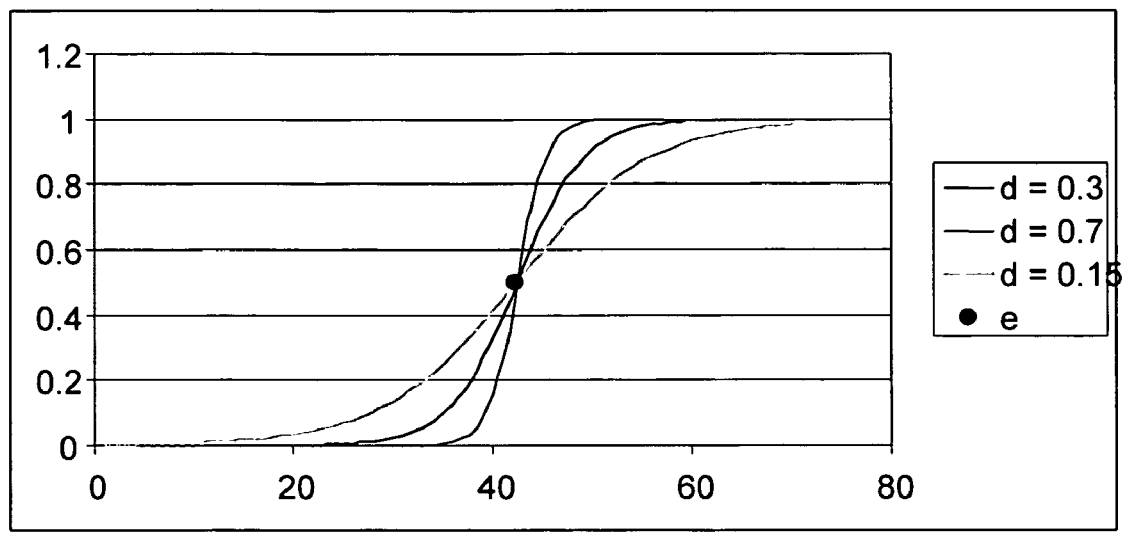
*All curves in Figure 7 have the same parameters except for d.*
Figure 8: Initial parameters shapes
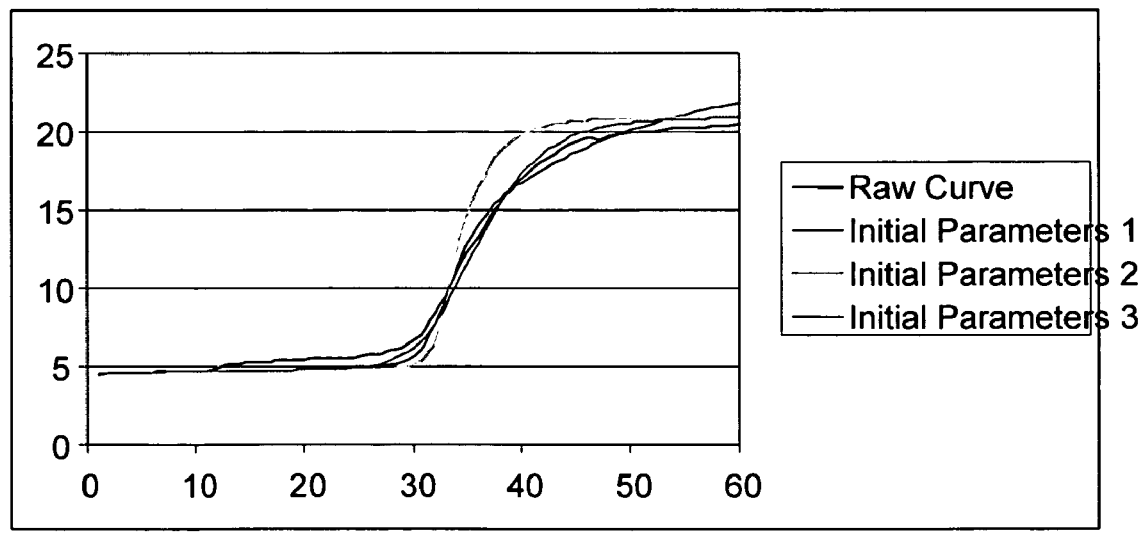

Figure 13: Approximation with and without the big spikes

FIG. 17a: Original Data

| X | Y | ypred | residual | \|residual-median\| | zi | |
|---|---|---|---|---|---|---|
| 1 | 5.01 | 5.04 | -0.03 | 0.148 | 0.46 | |
| 2 | 5.02 | 5.12 | -0.10 | 0.078 | 0.25 | |
| 3 | 5.03 | 5.20 | -0.17 | 0.012 | 0.04 | |
| 4 | 5.05 | 5.28 | -0.23 | 0.050 | 0.16 | |
| 5 | 5.08 | 5.36 | -0.28 | 0.104 | 0.33 | |
| 6 | 5.13 | 5.46 | -0.33 | 0.149 | 0.47 | |
| 7 | 5.22 | 5.58 | -0.36 | 0.183 | 0.57 | |
| 8 | 5.36 | 5.74 | -0.38 | 0.207 | 0.65 | |
| 9 | 5.59 | 5.99 | -0.40 | 0.224 | 0.70 | |
| 10 | 5.95 | 6.37 | -0.42 | 0.246 | 0.77 | |
| 11 | 11.52 | 6.98 | 4.54 | 4.715 | 14.77 | Outlier |
| 12 | 6.38 | 7.91 | -1.53 | 1.349 | 4.23 | Outlier |
| 13 | 10.65 | 9.25 | 1.40 | 1.579 | 4.95 | Outlier |
| 14 | 9.88 | 11.01 | -1.13 | 0.951 | 2.98 | |
| 15 | 12.55 | 13.10 | -0.55 | 0.374 | 1.17 | |
| 16 | 15.00 | 15.34 | -0.34 | 0.167 | 0.52 | |
| 17 | 17.45 | 17.50 | -0.06 | 0.122 | 0.38 | |
| 18 | 19.62 | 19.40 | 0.22 | 0.396 | 1.24 | |
| 19 | 21.35 | 20.95 | 0.40 | 0.578 | 1.81 | |
| 20 | 22.62 | 22.14 | 0.47 | 0.649 | 2.03 | |
| 21 | 23.48 | 23.03 | 0.45 | 0.628 | 1.97 | |
| 22 | 24.05 | 23.68 | 0.37 | 0.549 | 1.72 | |
| 23 | 24.41 | 24.15 | 0.26 | 0.441 | 1.38 | |
| 24 | 24.64 | 24.50 | 0.14 | 0.323 | 1.01 | |
| 25 | 24.78 | 24.75 | 0.03 | 0.205 | 0.64 | |
| 26 | 24.87 | 24.95 | -0.08 | 0.093 | 0.29 | |
| 27 | 24.92 | 25.11 | -0.19 | 0.012 | 0.04 | |
| 28 | 24.95 | 25.24 | -0.29 | 0.111 | 0.35 | |
| 29 | 24.97 | 25.35 | -0.38 | 0.204 | 0.64 | |
| 30 | 24.98 | 25.45 | -0.47 | 0.293 | 0.92 | |
| | | | -0.18 median | 0.215 MAD | | |
| X | Y | ypred | residual | \|residual-median\| | zi | |

LM Sigmoid Regression
| a | 4.96 |
|---|---|
| b | 0.08 |
| c | 18.25 |
| d | 0.35 |
| e | 11.52 |
| f | 0.45 |
| g | 15.03 |

FIG. 18a

Data with Outliers Removed

| X | Y | ypred |
|---|---|---|
| 1 | 5.01 | 5.01 |
| 2 | 5.02 | 5.02 |
| 3 | 5.03 | 5.04 |
| 4 | 5.05 | 5.07 |
| 5 | 5.08 | 5.10 |
| 6 | 5.13 | 5.15 |
| 7 | 5.22 | 5.23 |
| 8 | 5.36 | 5.35 |
| 9 | 5.59 | 5.54 |
| 10 | 5.95 | 5.86 |
| 14 | 9.88 | 10.15 |
| 15 | 12.55 | 12.37 |
| 16 | 15.00 | 14.91 |
| 17 | 17.45 | 17.45 |
| 18 | 19.62 | 19.67 |
| 19 | 21.35 | 21.40 |
| 20 | 22.62 | 22.65 |
| 21 | 23.48 | 23.49 |
| 22 | 24.05 | 24.03 |
| 23 | 24.41 | 24.38 |
| 24 | 24.64 | 24.61 |
| 25 | 24.78 | 24.75 |
| 26 | 24.87 | 24.85 |
| 27 | 24.92 | 24.91 |
| 28 | 24.95 | 24.96 |
| 29 | 24.97 | 25.00 |
| 30 | 24.98 | 25.03 |

LM Sigmoid Regression

| | |
|---|---|
| a | 4.99 |
| b | 0.02 |
| c | 19.61 |
| d | 0.53 |
| e | 15.92 |
| f | 0.25 |
| g | 2.49 |

FIG. 19a

Data with Corrected Values

| X | Y | ypred |
|---|---|---|
| 1 | 5.01 | 5.01 |
| 2 | 5.02 | 5.02 |
| 3 | 5.03 | 5.04 |
| 4 | 5.05 | 5.07 |
| 5 | 5.08 | 5.10 |
| 6 | 5.13 | 5.15 |
| 7 | 5.22 | 5.23 |
| 8 | 5.36 | 5.35 |
| 9 | 5.59 | 5.54 |
| 10 | 5.95 | 5.86 |
| 11 | 11.52 | 6.37 |
| 12 | 6.38 | 7.18 |
| 13 | 10.65 | 8.41 |
| 14 | 9.88 | 10.15 |
| 15 | 12.55 | 12.37 |
| 16 | 15.00 | 14.91 |
| 17 | 17.45 | 17.45 |
| 18 | 19.62 | 19.67 |
| 19 | 21.35 | 21.40 |
| 20 | 22.62 | 22.65 |
| 21 | 23.48 | 23.49 |
| 22 | 24.05 | 24.03 |
| 23 | 24.41 | 24.38 |
| 24 | 24.64 | 24.61 |
| 25 | 24.78 | 24.75 |
| 26 | 24.87 | 24.85 |
| 27 | 24.92 | 24.91 |
| 28 | 24.95 | 24.96 |
| 29 | 24.97 | 25.00 |
| 30 | 24.98 | 25.03 |

These values will be filled in by a cubic spline fit, or other interpolation fit, to the data.

LEVENBERG-MARQUARDT OUTLIER SPIKE REMOVAL METHOD

BACKGROUND OF THE INVENTION

The present invention relates generally to systems and methods for processing data representing sigmoid type curves or growth curves, and more particularly to systems and methods for detecting and correcting data spikes in real-time Polymerase Chain Reaction (PCR) amplification curves and other sigmoid or growth-type curves.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in real-time PCR, or kinetic PCR, to facilitate detection and quantification of the amplification process.

A typical kinetic PCR curve is shown in FIG. 2, where fluorescence intensity values (y-axis) are plotted vs. cycle number (x-axis) for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of quenched fluorescently labeled hybridization probes which only emit fluorescence signals after they are bound to a target nucleic acid sequence and subsequently degraded by the 5' to 3' nuclease activity of a DNA polymerase. Other examples include fluorescent signals generated during nucleic acid amplification where fluorescent dyes bind to double-stranded DNA and experience an increase in their fluorescence quantum yield.

During PCR data acquisition, artifacts such as air bubbles, gamma rays or incomplete mixing can cause outlier spikes in growth curves. An outlier spike or "spike" is a sudden jump in the signal that doesn't reflect the real growth. Spikes can affect further calculations done on the growth curves and therefore should be detected and corrected. FIG. 2 shows an example of a PCR growth curve including outlier spikes.

Current spike removal systems are available. However, these spike removal systems generally suffer from major deficiencies, such as an inability to correct most of the spikes wider than one cycle, an inability to correct early and late spikes, and a poor ability to detect and correct spikes in other various situations. Current spike removal systems also tend to have parameters that are often difficult to set.

Therefore it is desirable to provide outlier spike removal systems and methods that overcome the above and other problems. The systems and methods should provide a spike removal process that is more reliable and that includes fewer parameters or is parameter free.

BRIEF SUMMARY OF THE INVENTION

The present invention provides systems and methods for detecting and correcting for spikes in sigmoid or growth-type curves and curves representing other data set types. The present invention is particularly useful for detecting and correcting spikes in PCR data sets. According to the present invention, a robust estimation of the curve is calculated using a double sigmoid function, a variation of the Levenberg-Marquardt regression algorithm, and a statistical analysis of this result is used to detect the spikes.

According to the present invention, systems and methods are provided for identifying and removing spikes in data sets representing PCR growth curves or other sigmoid type curves or growth curves. A double sigmoid function with parameters determined by a Levenberg-Marquardt regression process is used in certain aspects to produce an approximation to the curve, and a statistical test such as a z-test is then used to identify spikes by identifying any data points in the data set that do not fit well with the approximation. Identified spike(s) are removed from the data set. The values of the data points removed may be replaced with data points determined by applying an interpolation algorithm to the remaining data points. In one aspect, a cubic spline interpolation process is used to find an approximation to the data set with the identified spike points removed. Interpolated values to replace the spike points are then calculated using the cubic spline interpolation approximation curve. Other spline interpolation processes may be used, such as first degree spline, second degree spline and trigonometric spline interpolation processes. Other interpolation processes might include an Aitken interpolation algorithm, a Bessell interpolation algorithm, an Everett interpolation algorithm, a Gauss interpolation algorithm, a Hermite interpolation algorithm, a Lagrange interpolation algorithm, a Newton-Cotes interpolation algorithm, an Osculating interpolation algorithm, or a Thiele's interpolation algorithm. In another aspect, other interpolation methods may be used, or the Levenberg-Marquardt regression process of the present invention, as applied to the sigmoid function and the data set with the spikes removed, may be used to determine interpolated values for the removed spike points.

According to one aspect of the present invention, a computer-implemented method is provided for removing outlier spikes from a data set for a Polymerase Chain Reaction (PCR) growth curve. The method typically includes receiving a data set for a PCR growth curve, calculating an approximation of the curve by applying a Levenberg-Marquardt (LM) regression process to the data set and a double sigmoid function to determine parameters of the function, and determining whether one or more data points are outlier spikes by applying a statistical test to the approximation and the data set. The method also typically includes removing the data values for an identified spike from the data set to produce a modified data set.

According to another aspect of the present invention, a Polymerase Chain Reaction (PCR) system is provided. The system typically includes a PCR analysis module that generates a PCR data set representing a PCR amplification curve, and an intelligence module adapted to process the PCR data set to identify and remove outlier spikes from the data set. The intelligence module is typically adapted to calculate an approximation of the curve by applying a Levenberg-Marquardt (LM) regression process to the data set and a double sigmoid function to determine parameters of the function and determine whether one or more data points are outlier spikes by applying a statistical test to the approximation and the data set. The intelligence module is also typically adapted to remove the data values for an identified spike from the data set to produce a modified data set.

According to yet another aspect of the present invention, a computer-readable medium is provided that includes code for controlling a processor to identify and remove outlier spikes in a data set for a Polymerase Chain Reaction (PCR) amplification curve. The code typically includes instructions to calculate an approximation of the curve by applying a Levenberg-Marquardt (LM) regression process to the data set and a double sigmoid function to determine parameters of the function, and determine whether one or more data points are outlier spikes by applying a statistical test to the approximation and the data set. The code also typically includes instructions to remove the data values for an identified spike from the data set to produce a modified data set.

In certain aspects, the double sigmoid fit function is of the form:

$$a + bx + \frac{c}{(1 + \exp^{-d(x-e)})(1 + \exp^{-f(x-g)})},$$

and one or more of the parameters a, b, c, d, e, f and g of the fit function are iteratively determined.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 2 illustrates a plot of a received data set and a robust approximation of the data set using a Levenberg-Marquardt process according to the present invention.

FIG. 3 illustrates a representation of three identified outliers in the plot of the data set and approximation shown in FIG. 2.

FIG. 4 illustrates a representation of interpolated data points for the identified outliers shown in FIG. 3.

FIG. 6 illustrates a decomposition of the double sigmoid equation including parameters a-g.

FIG. 7 shows the influence of parameter (d) on the curve and the position of (e), the x value of the inflexion point.

FIG. 8 shows an example of the three curve shapes for the different parameter sets.

DETAILED DESCRIPTION OF THE INVENTION

Figure 1:
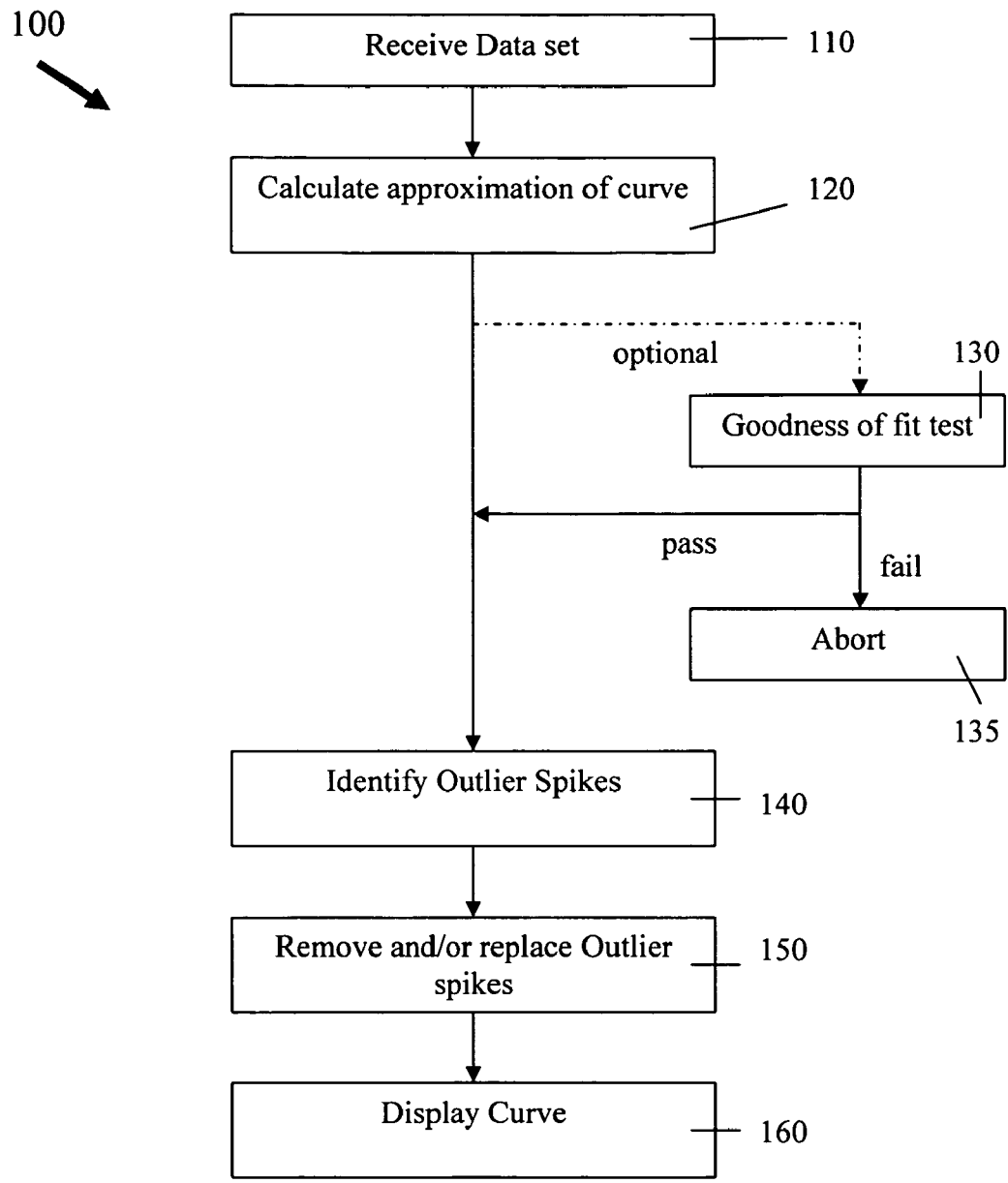
FIG. 1 illustrates a process flow for a spike identification and replacement process according to one embodiment of the present invention.

The present invention provides systems and methods for identifying and removing spikes in data sets representing PCR growth curves or other sigmoid type curves or growth curves. In certain aspects, a double sigmoid function with parameters determined by a Levenberg-Marquardt regression process is used to find an approximation to the curve. A statistical test is then used to identify spikes by determining those data points in the data set that do not fit well with the approximation. The identified spike(s) are removed from the data set and/or replaced with interpolated data points determined by using data points surrounding the identified spike(s) or the entire data set (less the spike points). In one aspect, for example, a spline interpolation (e.g., cubic spline, first degree spline, etc.) process is used to find an approximation to the data set with the identified spike points removed. Interpolated values to replace the spike points are then calculated using the spline interpolation approximation curve.

Data for a typical PCR growth curve can be represented in a two-dimensional coordinate system, for example, with PCR cycle number defining the x-axis and an indicator of accumulated polynucleotide growth defining the y-axis. An example of a plot of a PCR data set is shown in FIG. 2. Typically, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

Other processes that may provide similar sigmoid type curves or growth curves include bacterial processes, enzymatic processes and binding processes. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System", Clin Chem 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons", Nucleic Acids Research, 2002 30(6):26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

General Process Overview

According to the present invention, an embodiment of a process 100 for identifying and removing outlier spikes in a sigmoid type curve, such as a kinetic PCR amplification curve, is generally described with reference to FIG. 1. In step 110, a data set is received or otherwise acquired. An example of a plotted PCR data set is shown in FIG. 2, where the y-axis and x-axis represent fluorescence intensity and cycle number, respectively. In certain aspects, the data set should include data that is continuous and equally spaced along an axis. In certain aspects, baseline steps are removed prior to spike detection.

In the case where process 100 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For PCR data, the pair of coordinate values typically represents the cycle number and the fluorescence intensity value. After the data set has been received or acquired in step 110, the data set may be analyzed to identify and remove outlier spikes.

In step 120, an approximation of the curve is calculated. During this step, in one embodiment, a double sigmoid function with parameters determined by a Levenberg-Marquardt regression process is used to find an approximation of a curve representing the data set. The approximation is said to be "robust" as spikes have a minimal effect on the quality of the curve fit. FIG. 2 illustrates a plot of the received data set and a robust approximation of the data set determined by using a Levenberg-Marquardt regression process to determine the parameters of a double sigmoid function in according to the present invention.

In step 130, a goodness of fit of the approximation is determined or evaluated. This step is optional; in one aspect, the default process skips this step. If this step is executed, a goodness of fit test is run on the curve approximation calculated in step 120. This goodness of fit test in certain aspects includes either a Mean of Absolute Percentage Error (MAPE) test, a MAPE test with a baseline adjustment, or a Median of Absolute Deviation (MAD) test. If the fit isn't good enough, e.g., fails to satisfy a threshold criteria, the process is aborted in step 135. Otherwise, the process proceeds to step 140.

In step 140, outlier spikes are identified. Because the curve approximation calculated in step 120 is robust, points that are far from the approximation are likely to be spikes. According to one embodiment, a statistical test is performed to evaluate the likeliness that each point in the data set belongs to the curve approximation. In one aspect, a z-test is performed to identify those data points having a z-value that exceeds a specific threshold value. FIG. 3 illustrates a representation of three identified outliers in the plot of the data set and approximation shown in FIG. 2.

In step 150, the outliers identified in step 140 are removed and/or replaced. In one aspect, the identified outliers are removed from the data set. In another aspect, the outliers are replaced, for example, using an interpolation process, such as a cubic spline interpolation process, to calculate replacement data points using only the non-spiky points of the curve (i.e., using the data set with the outlier points identified in step 140 removed from the calculation). In another aspect, the Levenberg-Marquardt regression process of the present invention, as applied to the sigmoid function and the data set with the spikes removed, may be used to determine interpolated values for the removed spike points.

In step 160, the data set including the replacement points is displayed. FIG. 4 illustrates a representation of interpolated data points for the identified outliers shown in FIG. 3. In various aspects, a subset of the data shown in FIG. 4 may be displayed or other data may be displayed in addition to or alternatively to the data displayed in FIG. 4. Graphical displays may be rendered with a display device, such as a monitor screen or printer, coupled with the system that performed the analysis of FIG. 1, or data may be provided to a separate system for rendering on a display device.

Detailed Process Overview

Figure 5:
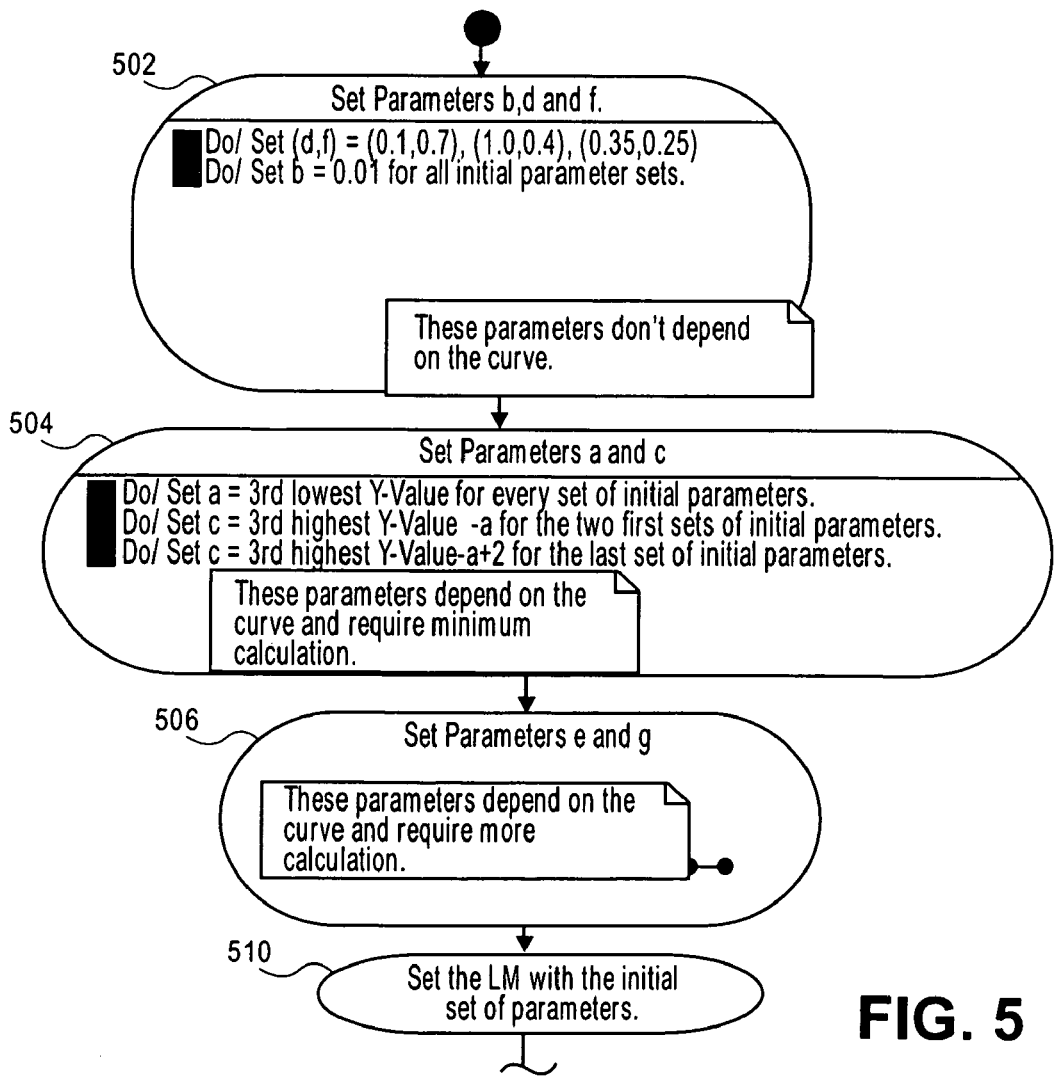
FIG. 5 illustrates a more detailed process flow for a spike identification and replacement process according to one embodiment of the present invention.
Figure 5:
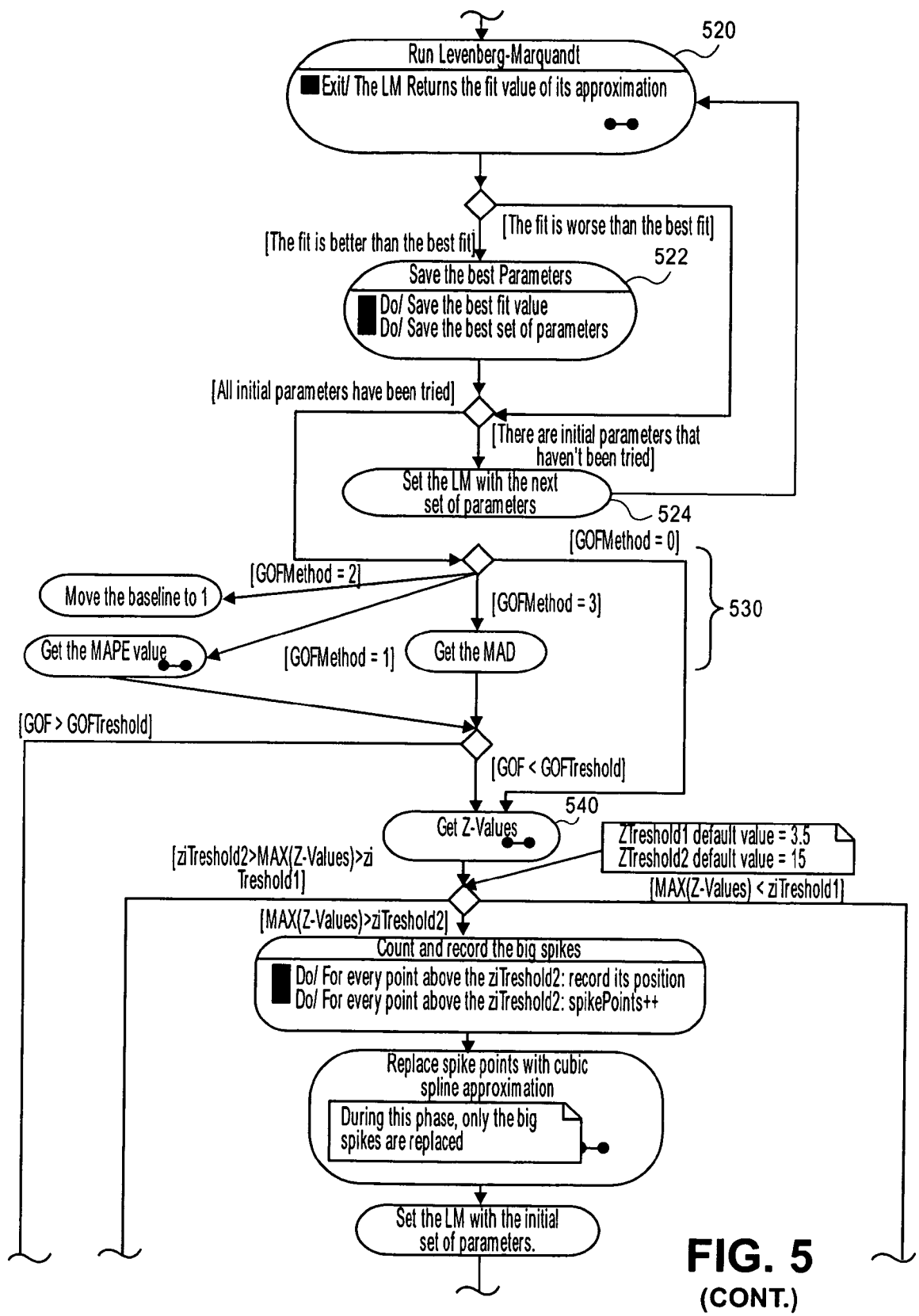
Figure 5:
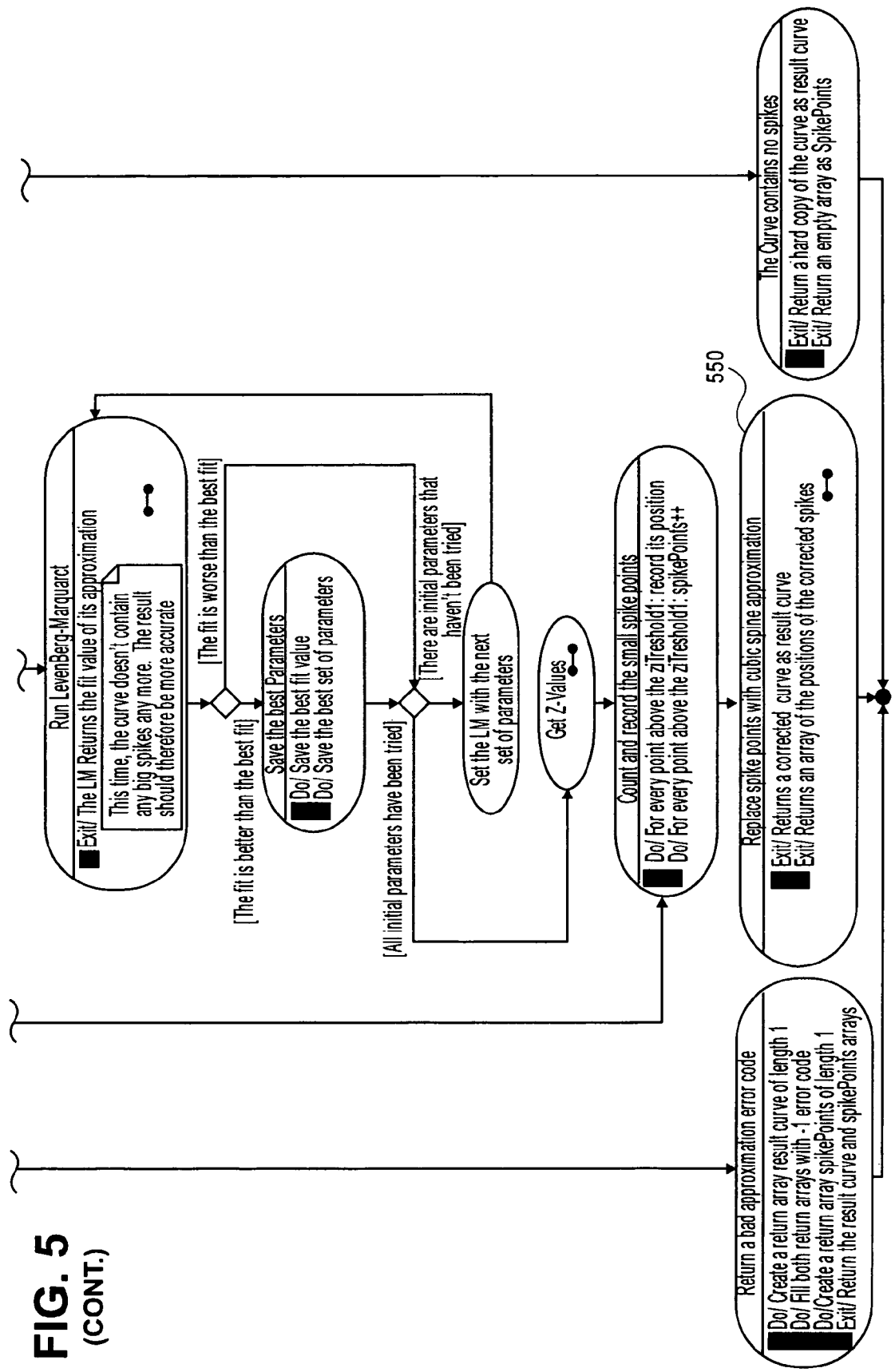

FIG. 5 illustrates a more detailed process flow for a spike identification and replacement process according to one embodiment of the present invention. As mentioned above, in one embodiment, a Levenberg-Marquardt (LM) method is used to calculate a robust curve approximation of the received data set. The LM method is a non-linear regression process; it is an iterative technique that minimizes the distance between a non-linear function and a data set. The process behaves like a combination of a steepest descent process and a Gauss-Newton process: when the current approximation doesn't fit well it behaves like the steepest descent process (slower but more reliable convergence), but as the current approximation becomes more accurate it will then behave like the Gauss-Newton process (faster but less reliable convergence). The LM regression method is widely used to solve non-linear regression problems.

In general, the LM regression method includes an algorithm that requires various inputs and provides output. In one aspect, the inputs include a data set to be processed, a function that is used to fit the data, and an initial guess for the parameters or variables of the function. The output includes a set of parameters for the function that minimizes the distance between the function and the data set.

According to one embodiment, the fit function used in the LM method is a double sigmoid of the form:

$$a + bx + \frac{c}{(1 + \exp^{-d(x-e)})(1 + \exp^{-f(x-g)})} \quad (4)$$

The choice of this equation as the fit function is based on its flexibility and its ability to fit the different curve shapes that a typical PCR curve or other double sigmoid curve may take. One skilled in the art will appreciate that other fit functions may be used as desired.

The double sigmoid equation (4) has 7 parameters: a, b, c, d, e, f and g. The equation can be decomposed into a sum of a constant, a slope and a double sigmoid. The double sigmoid itself is the multiplication of two sigmoids. FIG. 6 illustrates a decomposition of the double sigmoid equation (4). The parameters d, e, f and g determine the shape of the two sigmoids. To show their influence on the final curve, consider the single sigmoid:

$$\frac{1}{1+\exp^{-d(x-e)}}, \quad (5)$$

where the parameter d determines the "sharpness" of the curve and the parameter e determines the x-value of the inflexion point. FIG. 7 shows the influence of the parameter d on the curve and of the parameter e on the position of the x value of the inflexion point. Table 1, below, describes the influence of the parameters on the double sigmoid curve.

TABLE 1

Double sigmoid parameters description

| Parameter | Influence on the curve |
|---|---|
| a | Value of y at x = 0 |
| b | baseline and plateau slope |
| c | AFI of the curve |
| d | "sharpness" of the first sigmoid (See Error! Reference source not found. 7) |
| e | position of the inflexion point of the first sigmoid (See Error! Reference source not found. 7) |
| f | "sharpness" of the second sigmoid |
| g | position of the inflexion point of the second sigmoid |

In one aspect, the "sharpness" parameters d and f of the double sigmoid equation should be constrained in order to prevent the curve from taking unrealistic shapes. Therefore, in one aspect, any iterations where d<−1 or d>1.1 or where f<−1 or f>1.1 is considered unsuccessful. In other aspects, different constraints on parameters d and f may be used.

Because the Levenberg-Marquardt algorithm is an iterative algorithm, an initial guess for the parameters of the function to fit is typically needed. The better the initial guess, the better the approximation will be and the less likely it is that the algorithm will converge towards a local minimum. Due to the complexity of the double sigmoid function and the various shapes of PCR curves or other growth curves, one initial guess for every parameter may not be sufficient to prevent the algorithm from sometimes converging towards local minima. Therefore, in one aspect, multiple (e.g., three or more) sets of initial parameters are input and the best result is kept. In one aspect, most of the parameters are held constant across the multiple sets of parameters used; only parameters c, d and f may be different for each of the multiple parameter sets. FIG. 8 shows an example of the three curve shapes for the different parameter sets. The choice of these three sets of parameters is indicative of three possible different shapes of curves representing PCR data. It should be understood that more than three sets of parameters may be processed and the best result kept.

As shown in FIG. 5, the initial input parameters of the LM method are identified in step 510. These parameters may be input by an operator or calculated. According to one aspect, the parameters are determined or set according to steps 502, 504 and 506 as discussed below.

Calculation of initial parameter (a):

The parameter (a) is the height of the baseline; its value is the same for all sets of initial parameters. In one aspect, in step 504 the parameter (a) is assigned the 3rd lowest y-axis value, e.g., fluorescence value, from the data set. This provides for a robust calculation. In other aspects, of course, the parameter (a) may be assigned any other fluorescence value as desired such as the lowest y-axis value, second lowest value, etc.

Calculation of initial parameter (b):

The parameter (b) is the slope of the baseline and plateau. Its value is the same for all sets of initial parameters. In one aspect, in step 502 a static value of 0.01 is assigned to (b) as ideally there shouldn't be any slope. In other aspects, the parameter (b) may be assigned a different value, for example, a value ranging from 0 to about 0.5.

Calculation of initial parameter (c):

The parameter (c) represents the absolute intensity of the curve; for PCR data the parameter (c) typically represents the AFI of the curve. To calculate the AFI, the height of the plateau is important. To calculate this in a robust way, in one aspect, the 3rd highest y-axis value, e.g., fluorescence value, is assigned as the plateau height in step 504. Then, the AFI=height of plateau−height of baseline=3rd highest fluorescence value−(a). In other aspects, the parameter (c) may be assigned any other fluorescence value as desired, such as the highest y-axis value, next highest, etc.

As shown in FIG. 8, for the last two sets of parameters, c=AFI. For the first set of parameters, c=AFI+2. This change is due to the shape of the curve modeled by the first set of parameters, which doesn't have a plateau.

Calculation of parameters (d) and (f):

The parameters (d) and (f) define the sharpness of the two sigmoids. As there is no way of giving an approximation based on the curve for these parameters, in one aspect three static representative values are used in step 502. It should be understood that other static or non-static values may be used for parameters (d) and/or (f). These pairs model the most common shapes on PCR curves encountered. Table 2, below, shows the values of (d) and (f) for the different sets of parameters as shown in FIG. 8.

TABLE 2

Values of parameters d and f

| Parameter set number | Value of d | Value of f |
|---|---|---|
| 1 | 0.1 | 0.7 |
| 2 | 1.0 | 0.4 |
| 3 | 0.35 | 0.25 |

Calculation of parameters (e) and (g):

In step 506, the parameters (e) and (g) are determined. The parameters (e) and (g) define the inflexion points of the two sigmoids. In one aspect, they both take the same value across all the initial parameter sets. Parameters (e) and (g) may have the same or different values. To find an approximation, in one aspect, the x-value of the first point above the mean of the intensity, e.g., fluorescence, (which isn't a spike) is used. A process for determining the value of (e) and (g) according to this aspect is shown in more detail in FIG. 9 and discussed below.

Figure 9:
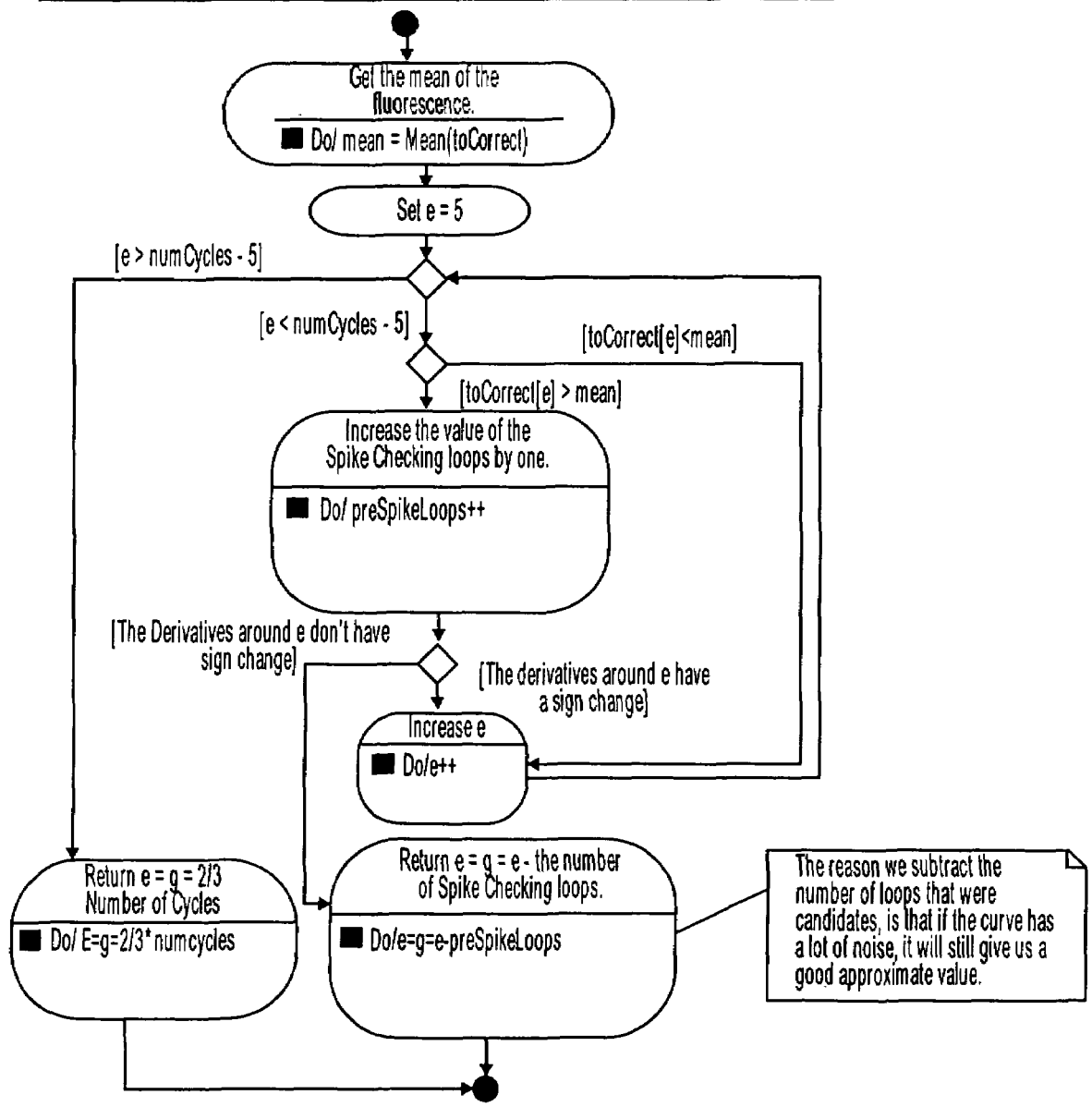
FIG. 9 illustrates a process for determining the value of double sigmoid equation parameters (e) and (g) according to one aspect.

In FIG. 9, initially, the mean of the curve (e.g., fluorescence intensity) is determined. Next, the first data point above the mean is identified. It is then determined whether:

a. that point does not lie near the beginning, e.g., within the first 5 cycles, of the curve;

b. that point does not lie near the end, e.g., within the 5 last cycles, of the curve; and c. the derivatives around the point (e.g., in a radius of 2 points around it) do not show any change of sign. If they do, the point is likely to be a spike and should therefore be rejected.

Table 3, below, shows examples of initial parameter values as used in FIG. 8 according to one aspect.

TABLE 3

Initial parameters values:

| | Initial parameter set number | | |
|---|---|---|---|
| | 1 | 2 | 3 |
| Value of a | 3$^{rd}$ lowest fluorescence value | 3$^{rd}$ lowest fluorescence value | 3$^{rd}$ lowest fluorescence value |
| Value of b | 0.01 | 0.01 | 0.01 |
| Value of c | 3$^{rd}$ highest fluorescence value - a + 2 | 3$^{rd}$ highest fluorescence value - a | 3$^{rd}$ highest fluorescence value - a |
| Value of d | 0.1 | 1.0 | 0.35 |
| Value of e | X of the first non-spiky point above the mean of the fluorescence | X of the first non-spiky point above the mean of the fluorescence | X of the first non-spiky point above the mean of the fluorescence |
| Value of f | 0.7 | 0.4 | 0.25 |
| Value of g | X of the first non-spiky point above the mean of the fluorescence | X of the first non-spiky point above the mean of the fluorescence | X of the first non-spiky point above the mean of the fluorescence |

Returning to FIG. 5, once all the parameters are set in step 510, a LM process 520 is executed using the input data set, function and parameters. Traditionally, the Levenberg-Marquardt method is used to solve non-linear least-square problems. The traditional LM method calculates a distance measure defined as the sum of the square of the errors between the curve approximation and the data set. However, when minimizing the sum of the squares, it gives outliers an important weight as their distance is larger than the distance of non-spiky data points, often resulting in inappropriate curves or less desirable curves. Therefore, according to one aspect of the present invention, the distance between the approximation and the data set is computed by minimizing the sum of absolute errors as this does not give as much weight to the outliers. In this aspect, the distance between the approximation and data is given by:

$$\text{distance} = \Sigma |y_{data} - y_{approximation}|. \quad (1)$$

As above, in one aspect, each of the multiple (e.g., three) sets of initial parameters are input and processed and the best result is kept as shown in steps 522 and 524, where the best result is the parameter set that provides the smallest or minimum distance in equation (1). In one aspect, most of the parameters are held constant across the multiple sets of parameters; only c, d and f may be different for each set of parameters. It should be understood that any number of initial parameter sets may be used.

Figure 10:
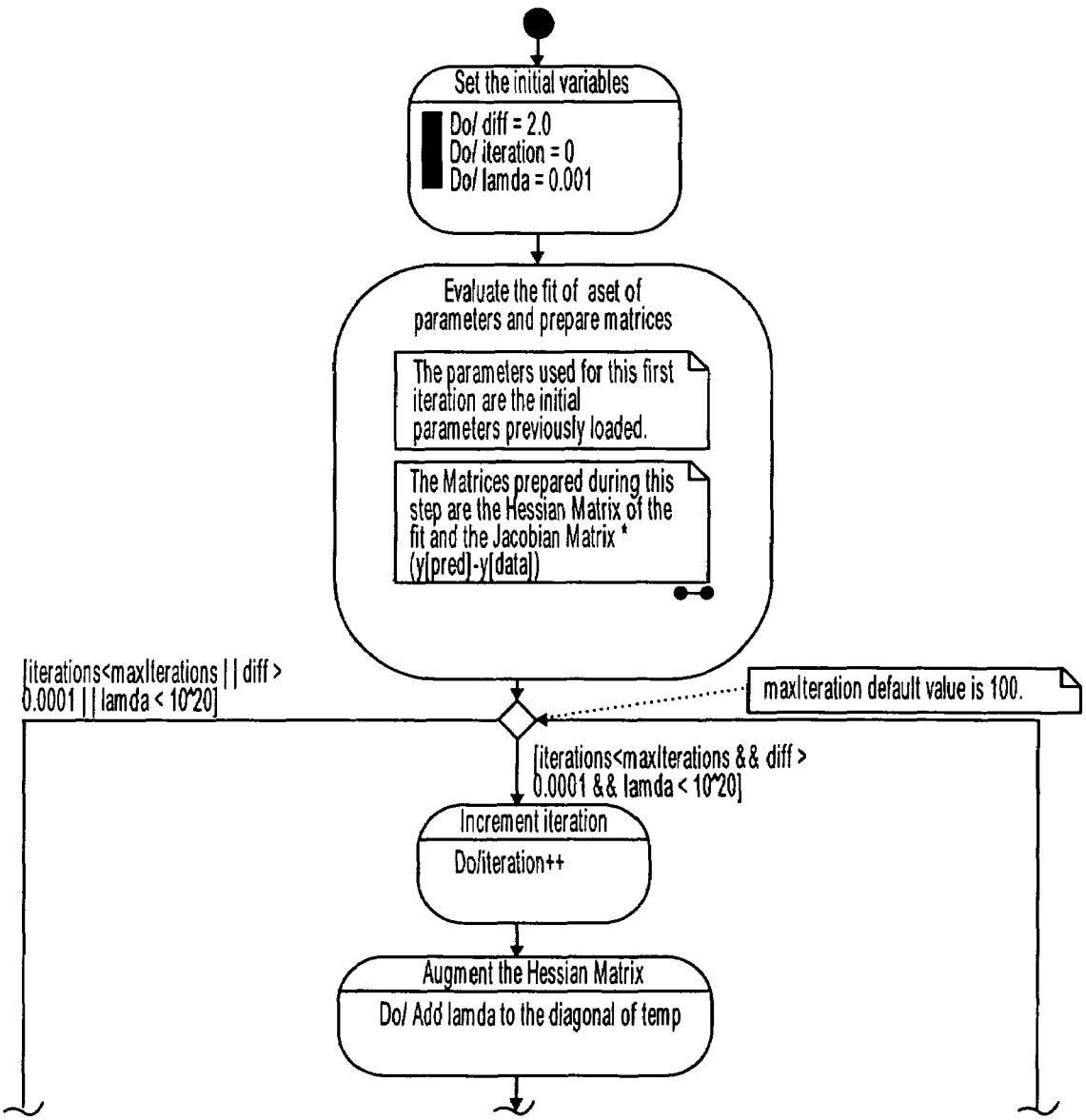
FIG. 10 illustrates a process flow of Levenberg-Marquardt process for an initial set of parameters.
Figure 10:
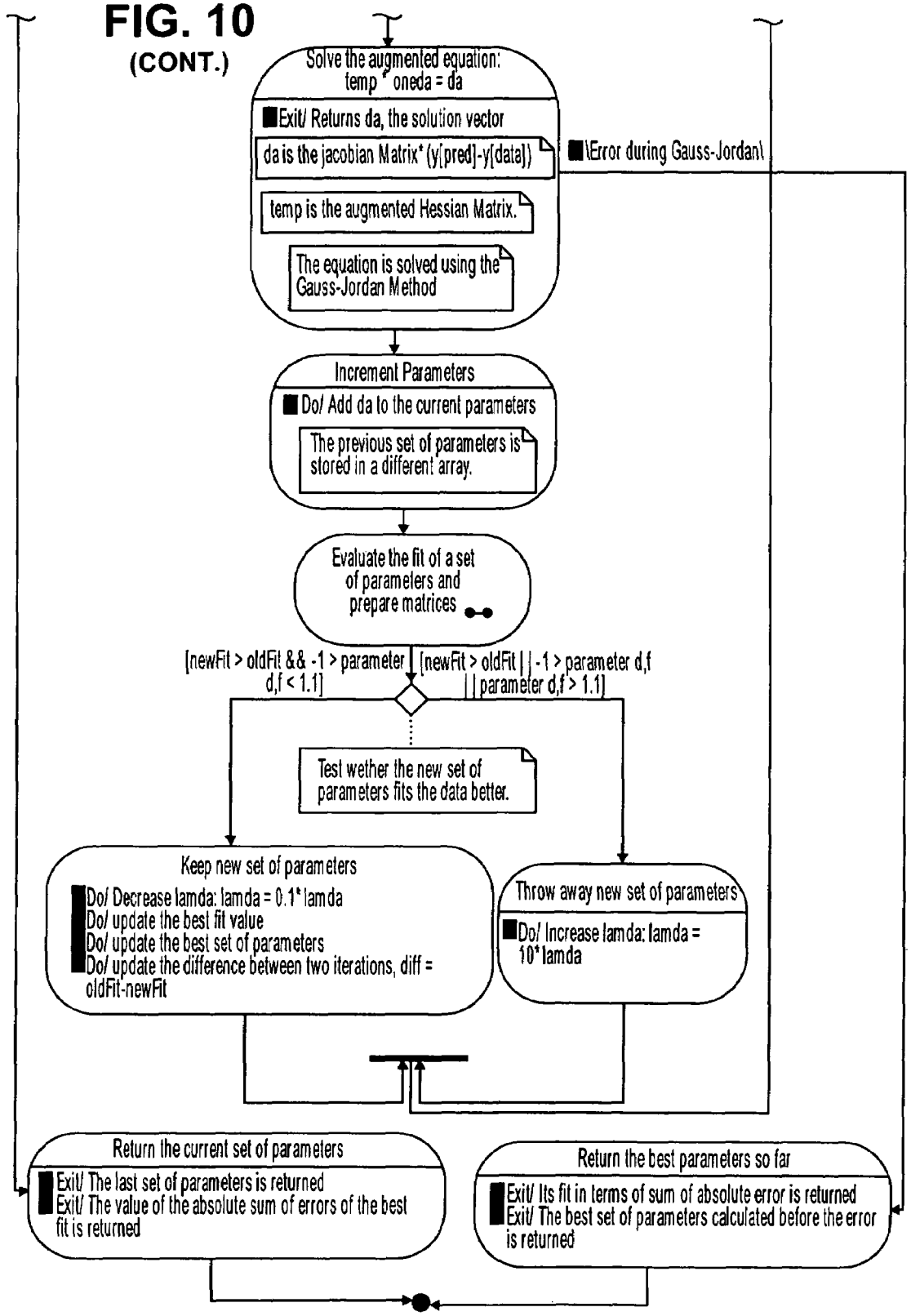

FIG. 10 illustrates a process flow of LM process 520 for a set of parameters according to the present invention. As explained above, the Levenberg-Marquardt method can behave either like a steepest descent process or like a Gauss-Newton process. Its behavior depends on a damping factor λ. The larger λ is, the more the Levenberg-Marquardt algorithm will behave like the steepest descent process. On the other hand, the smaller λ is, the more the Levenberg-Marquardt algorithm will behave like the Gauss-Newton process. In one aspect, λ is initiated at 0.001. It should be appreciated that λ may be initiated at any other value, such as from about 0.000001 to about 1.0.

As stated before, the Levenberg-Marquardt method is an iterative technique. According to one aspect, as shown in FIG. 10 the following is done during each iteration:

1. The Hessian Matrix (H) of the precedent approximation is calculated.
2. The transposed Jacobian Matrix ($J^T$) of the precedent approximation is calculated.
3. The distance vector (d) of the precedent approximation is calculated.
4. The Hessian Matrix diagonal is augmented by the current damping factor λ:

$$H_{aug} = H\lambda \quad (2)$$

5. Solve the augmented equation:

$$H_{aug}x = J^T d \quad (3)$$

6. The solution x of the augmented equation is added to the parameters of the function.
7. Calculate the distance between the new approximation and the curve.
8. If the distance with this new set of parameters is smaller than the distance with the previous set of parameters:
   The iteration is considered successful.
   Keep or store the new set of parameters.
   Decrease the damping factor λ, e.g., by a factor 10.
   If the distance with this new set of parameters is larger than the distance with the previous set of parameters:
   The iteration is considered unsuccessful.
   Throw away the new set of parameters.
   Increase the damping factor λ, e.g., by a factor of 10.

In one aspect, the LM process of FIG. 10 iterates until one of the following criteria is achieved:

1. It has run for a specified number, N, of iterations. This first criterion prevents the algorithm from iterating indefinitely. For example, in one aspect as shown in FIG. 10, the default iteration value N is 100. 100 iterations should be plenty for the algorithm to converge if it can converge. In general, N can range from fewer than 10 to 100 or more.
2. The difference of the distances between two successful iterations is smaller than a threshold value. e.g., 0.0001. When the difference becomes very small, the desired precision has been achieved and continuing to iterate is pointless as the solution won't become significantly better.
3. The damping factor λ exceeds a specified value, e.g., is larger than $10^{20}$. When λ becomes very large, the algorithm won't converge any better than the current solution, therefore it is pointless to continue iterating. In general, the specified value can be significantly smaller or larger than $10^{20}$.

Returning to FIG. 5, once an approximation of the curve has been determined and the best set of parameters identified, it may be useful to check whether the approximation is likely to match the data set. According to one aspect, in step 530 an optional goodness of fit test is applied. In one aspect, a system operator may manually select or pre-select whether to apply a goodness of fit test and which type of test is appropriate. For example, an operator may chose to not run the test (option 0), or to run one of a MAPE test (option 1), a MAPE test with a baseline adjustment (option 2), or a MAD test (option 3).

Figure 11:
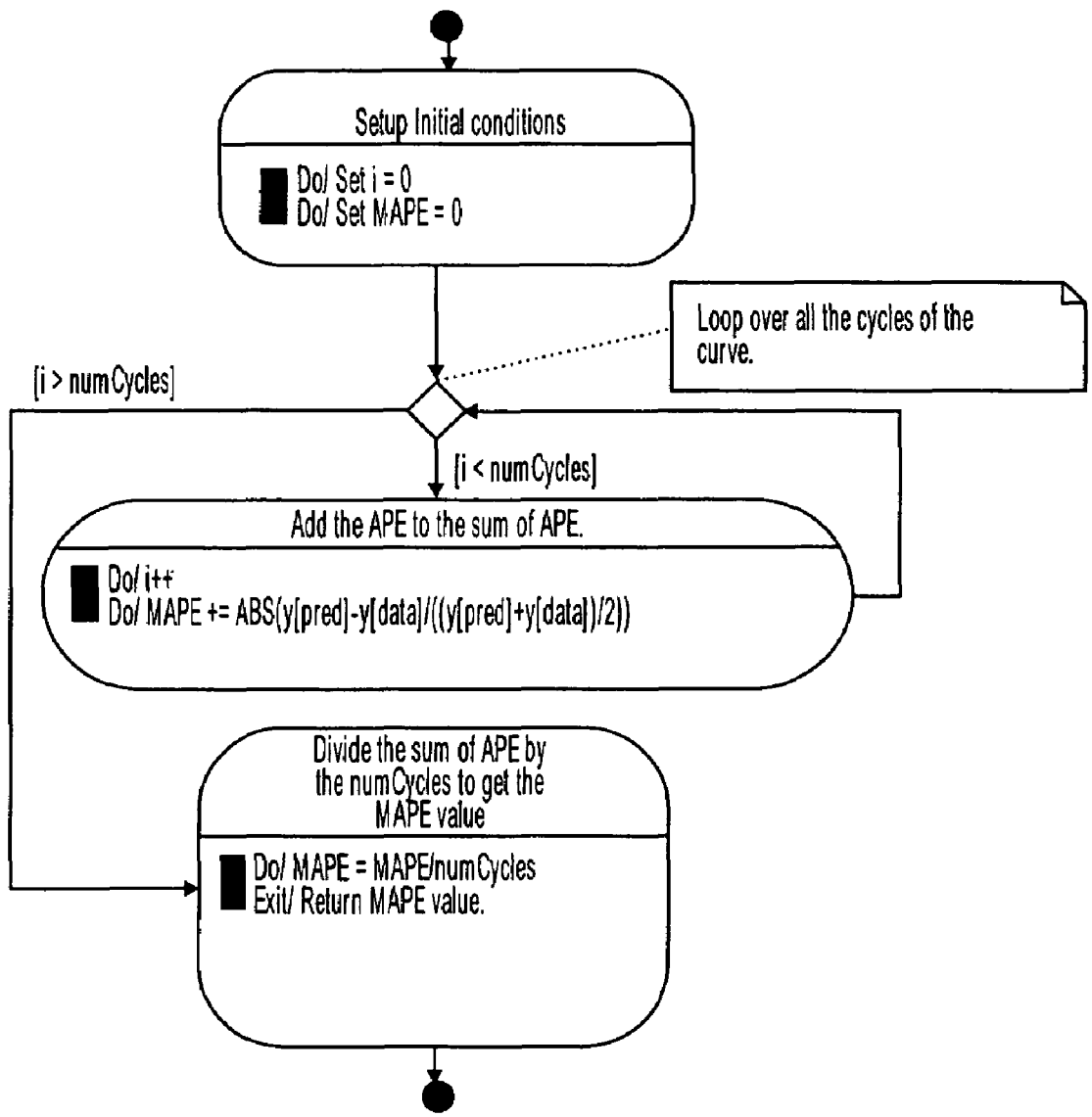
FIG. 11 illustrates a calculation of a MAPE value according to one aspect.

A MAPE test uses the Mean Absolute Percentage Error to determine whether an approximation is likely to match a data set. In one aspect, the calculation of the MAPE is performed as shown in FIG. 11 and discussed below:

1. Calculate the Absolute Percentage Error for every point:

$$APE = ABS\left(\frac{y_{approximation} - y_{data}}{\frac{y_{approximation} + y_{data}}{2}}\right). \quad (6)$$

2. Take the mean of the APE.

$$MAPE = \frac{\sum_{curve} APE}{curve.length}. \quad (7)$$

where the curve.length is the number of discrete data intervals along the x-axis in the data set, e.g., cycles in a PCR data set, that is being processed. The MAPE test, however, may not produce good results when the fluorescence value goes below zero. Also, it may be difficult to set a MAPE threshold that allows for both positive and negative curves to be accepted as a good fit. Further, the MAPE test results depend on the height of the curve. It should be noted that the APE value produced in equation (6) is actually a fraction; to convert to a percentage error, one would multiply the APE value from equation (6) by 100.

The MAPE test with baseline adjustment can be used to evaluate the goodness of fit of a curve. The idea of this test is to have every curve at the same height to prevent negative y-axis, e.g., fluorescence, values and high curves having good goodness of fit values due to their height and not their shape. In one aspect, this variant of the MAPE test proceeds as follows:

1. Find the minimum fluorescence value of the curve.

2. Add 1—the minimum fluorescence value of the curve to every point in the data set.

3. Perform a MAPE test as described above with reference to FIG. 11.

This variant of the MAPE test solves some of the problems encountered using a standard MAPE test, but it tends to reject curves of high fluorescence value and it is still hard to find a good threshold to accept negative and positive samples good approximations.

The MAD test evaluates the goodness of fit of a curve by calculating its Median Absolute Deviation and comparing it with a threshold value. As the MAD test is a robust method, it won't be problematic if there are spikes, however, it may be difficult to determine a good threshold. Aspects of a MAD test can be found below with reference to its use in the z-test.

Returning to FIG. 5, once the LM process has returned a best fit curve and parameters, in step 540, a statistical test is performed to identify spike points in the data set. In one aspect, a z-test is performed on every point of the curve to produce a z-value. The hypothesis tested is that every point of the curve belongs to the calculated approximation. If the z-value of a point is larger than a threshold, the point is then considered a spike. In another aspect, a two-pass z-test is performed, wherein two sequential z-tests are performed with two different threshold values. On the second pass, spikes identified in the first pass with a larger threshold are removed from the data set, and the second z-test is performed with a lower threshold.

Figure 12:
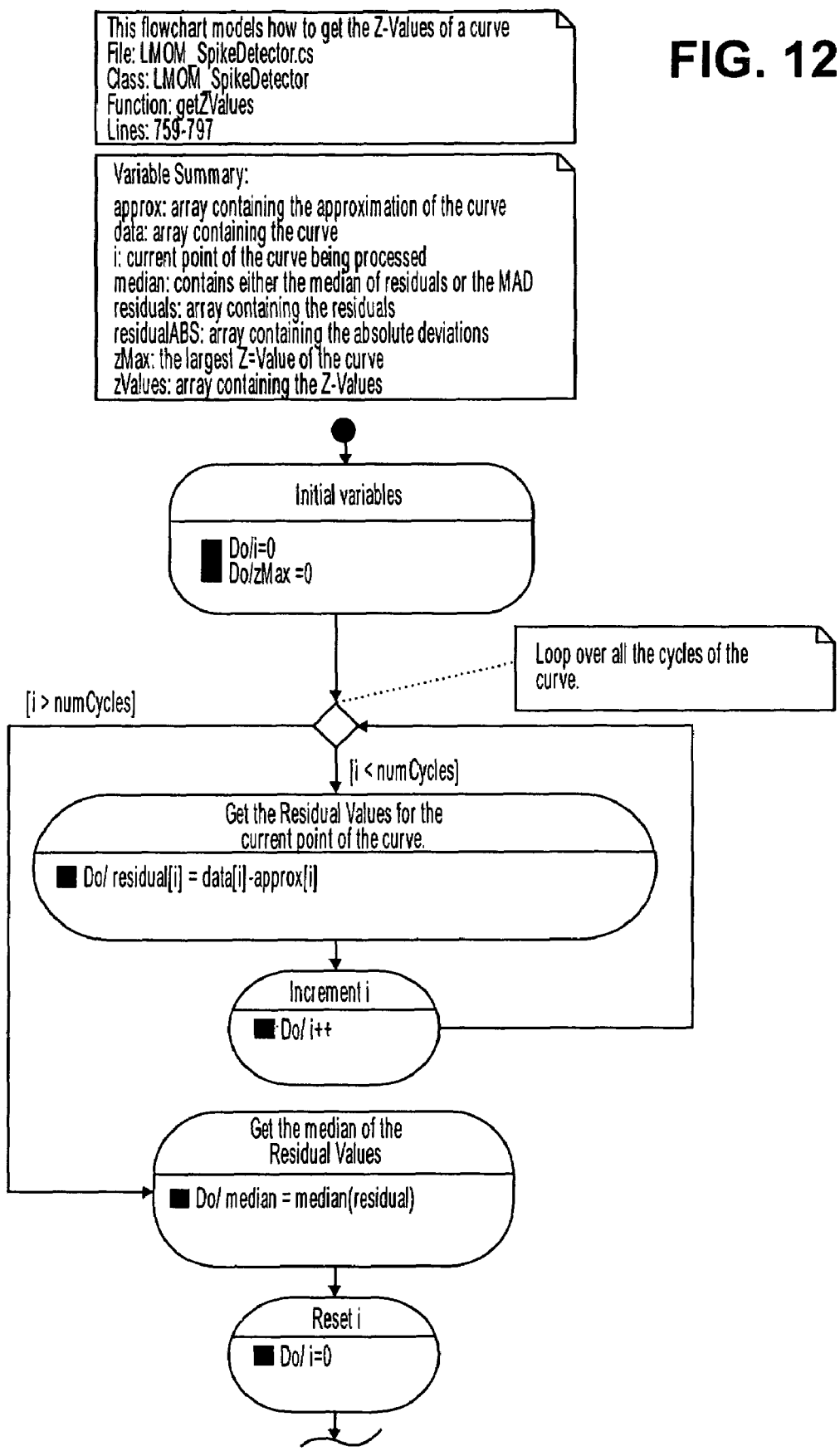
FIG. 12 illustrates a process for calculating the z-values of an approximation curve and a data set according to one aspect.
Figure 12:
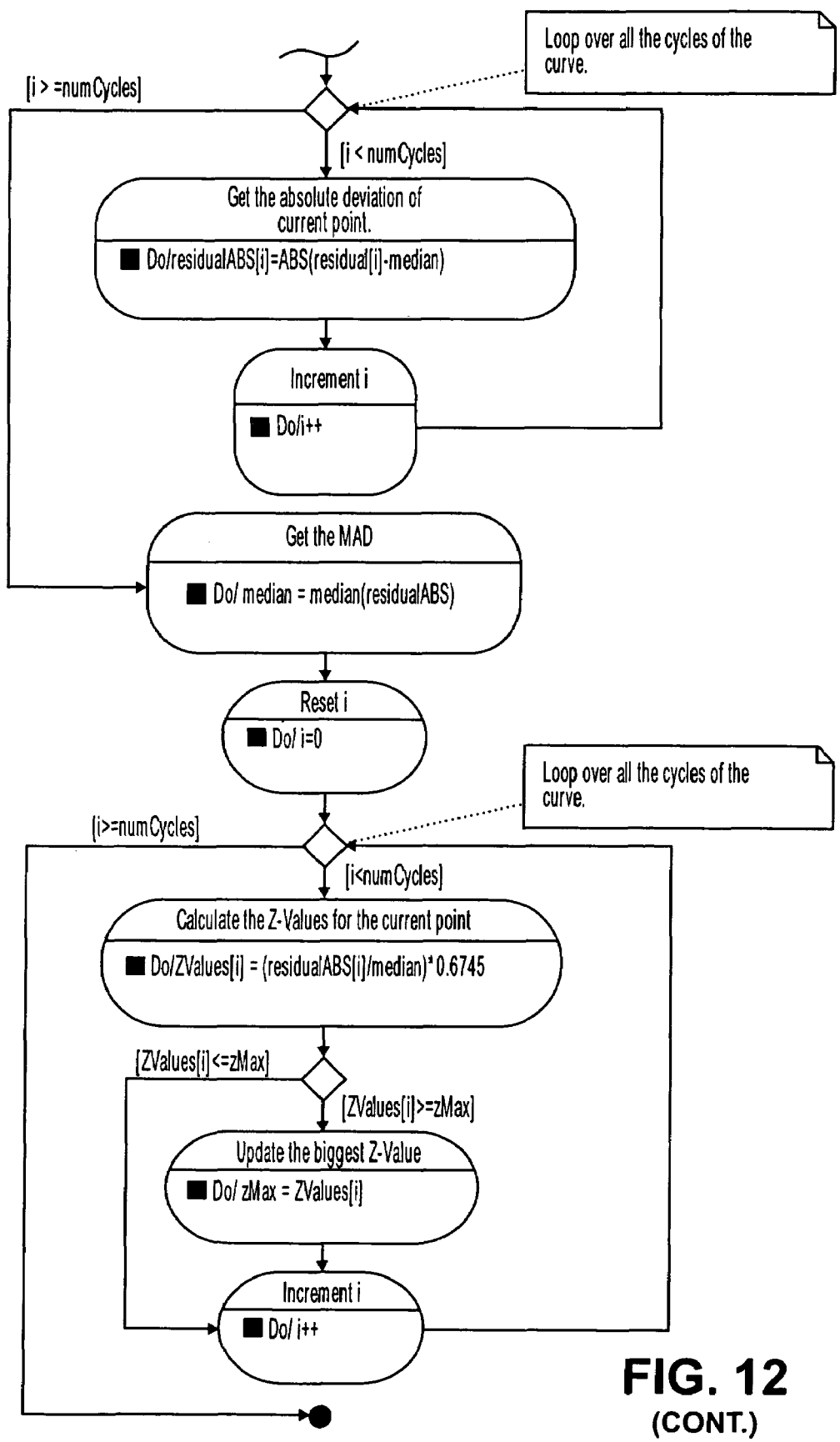

According to one aspect, calculation of the z-values is performed as shown in FIG. 12 and discussed with reference to the following process steps:

1. Calculation of the residuals:
   for every point, calculate the distance between the data and the approximation:

$$\text{Residual}(y) = y_{data} - y_{approximation}. \quad (8)$$

2. Calculation of the Absolute deviation for every point:
   Calculate the median of the residuals
   For every point calculate the Absolute Deviation (AD):

$$AD = ABS(\text{Residual} - \text{median}). \quad (9)$$

3. Calculation of the Median of Absolute Deviation (MAD):

$$MAD = \text{Median}(AD). \quad (10)$$

4. Calculation of the Z-Values for every point:

$$Z\text{-Value} = AD/MAD*0.6745. \quad (11)$$

2-pass Z-Test

In another aspect, as the approximation calculated is influenced by spikes, a 2-pass z-test with two different thresholds is performed as shown in step 540 of FIG. 5, and with reference to the following process steps:

1. Perform a z-test (e.g., FIG. 12) with a high threshold, e.g., a threshold of 10 or 15, to identify any big spikes.

2. Replace the identified big spikes in the data set, e.g., using a cubic spline or other interpolation process (e.g., FIG. 16).

3. Calculate a new approximation of the curve without the big spikes in the data set, e.g., step 520 of FIG. 5 as shown in FIG. 10. The Levenberg-Marquardt regression algorithm is again used and initialized using the three sets of initial parameters; only the best approximation is kept.

4. Perform a second Z-Test with a lower threshold, e.g., a threshold of 3 or 3.5, to identify any smaller spikes.

5. Replace the smaller spikes in the data set, e.g., using a cubic spline or other interpolation process.

Figure 13:
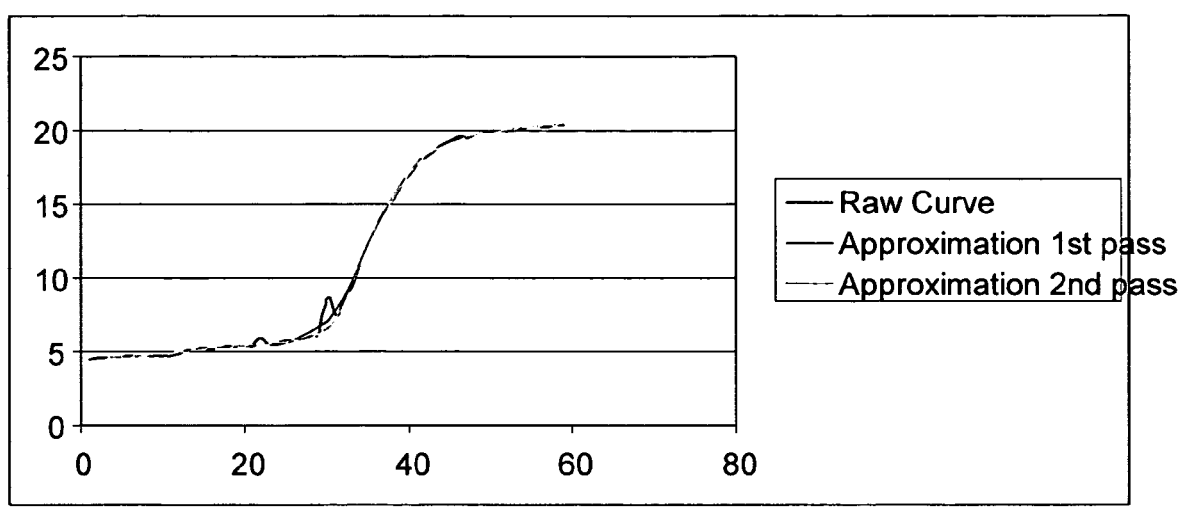
FIG. 13 shows an example of an approximation curve with and without "big" spikes.

FIG. 13 shows an example of an approximation with and without the big spikes.

Figure 16:
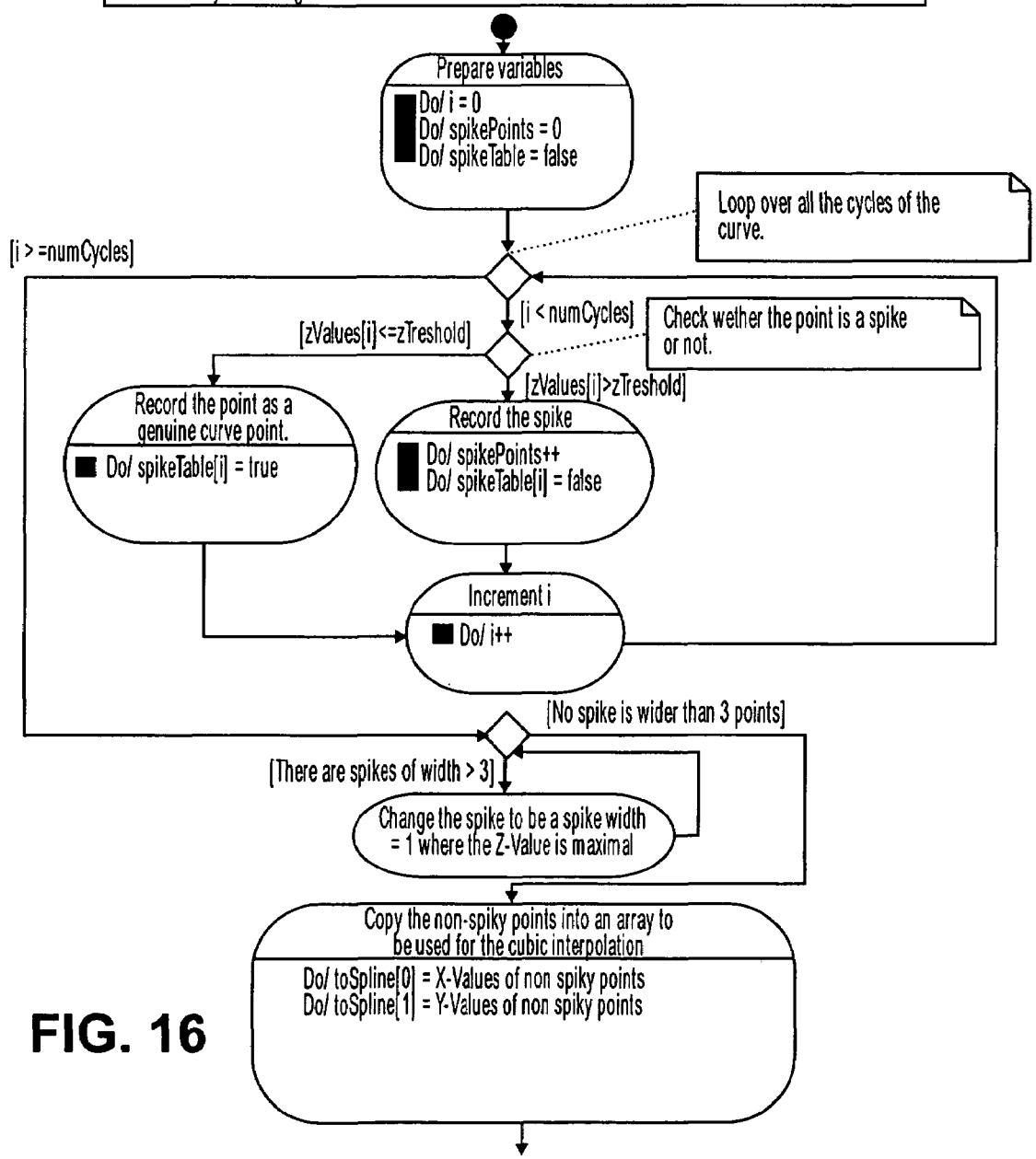
FIG. 16 shows an example of a method to replace identified spike points according to one embodiment.
Figure 16:
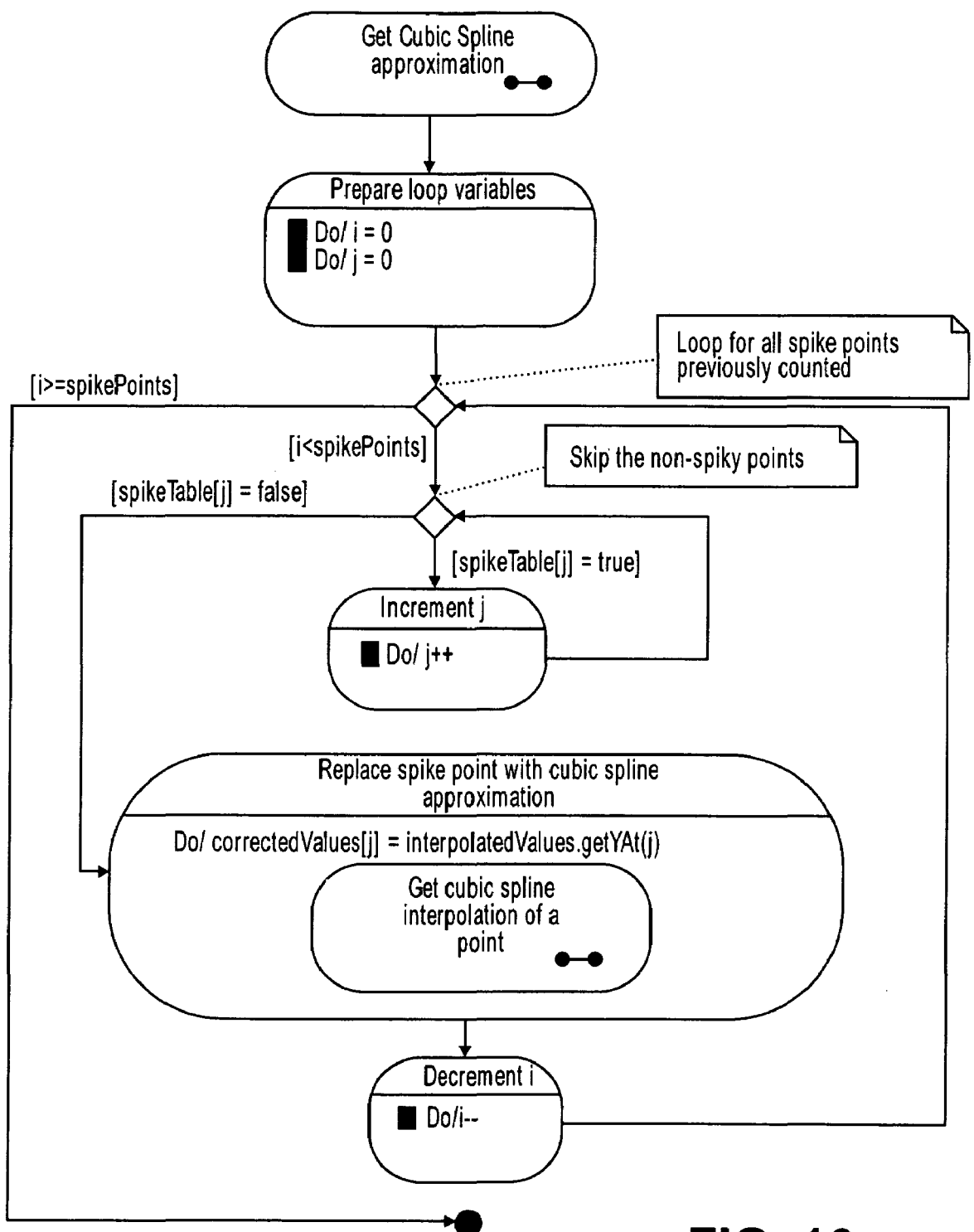

Returning to FIG. 5, in step 550, once the spike points have been identified using a z-test (or a two-pass z-test), the identified points are replaced with an approximation of their expected value, i.e., what the value would be without the artifact that caused the erroneous data. Where a two-pass z-test is used, the points identified in the first pass are also replaced before the second pass. FIG. 16 shows an example of a method to replace identified spike points according to one aspect. First, the spike points are identified using a z-test or other statistical test. Next, a cubic spline or other interpolation or approximation of the curve is calculated using the data set without the spiky points (the identified spikes are removed from the data set for this calculation). Thereafter, the values of the data points corresponding to the removed spike points are replaced with values interpolated using the cubic spline approximation. Additional details and aspects can be found in FIG. 16 and below.

Figure 14:
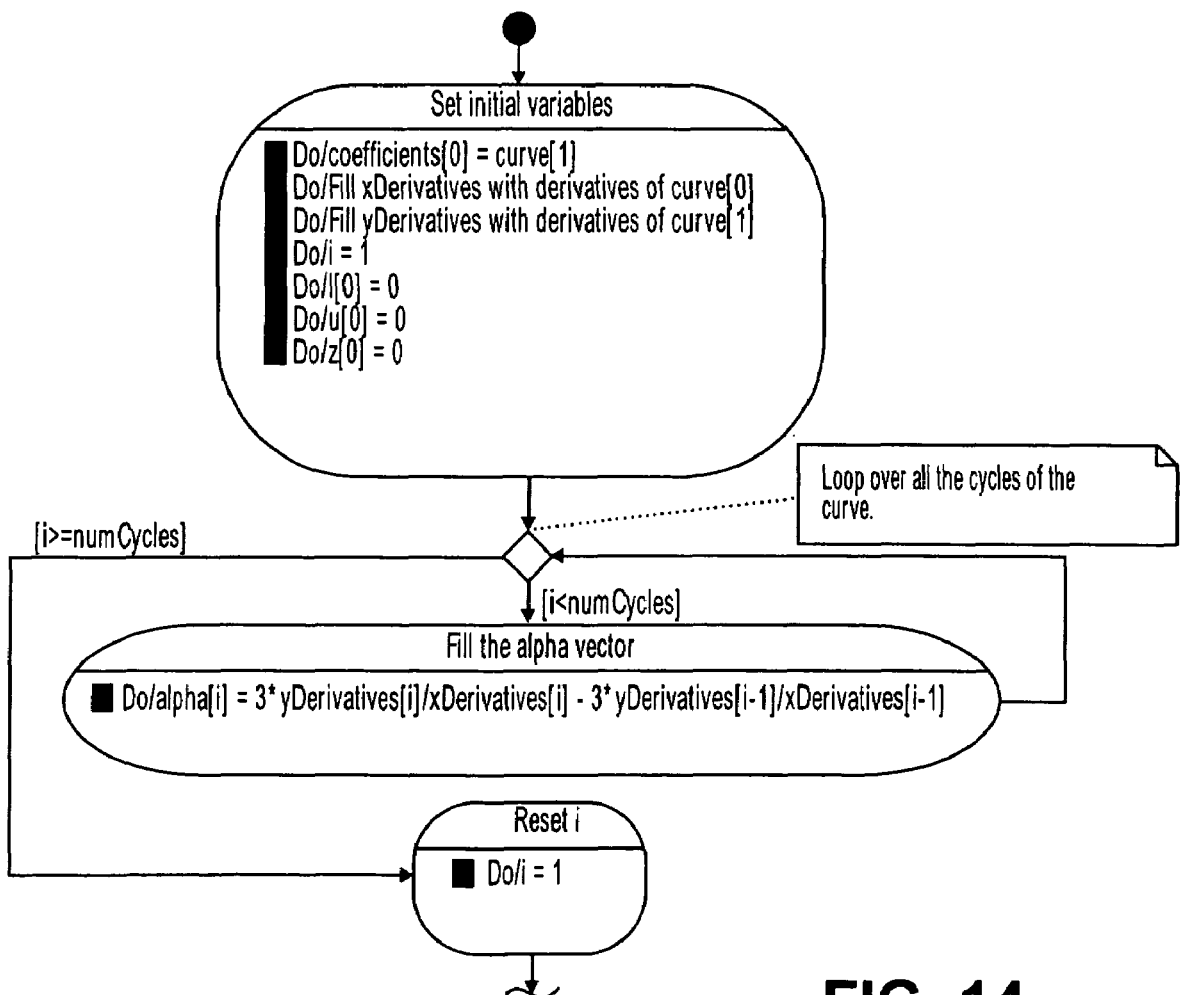
FIG. 14 illustrates a flowchart of a cubic spline interpolation calculation process according to one embodiment.
Figure 14:
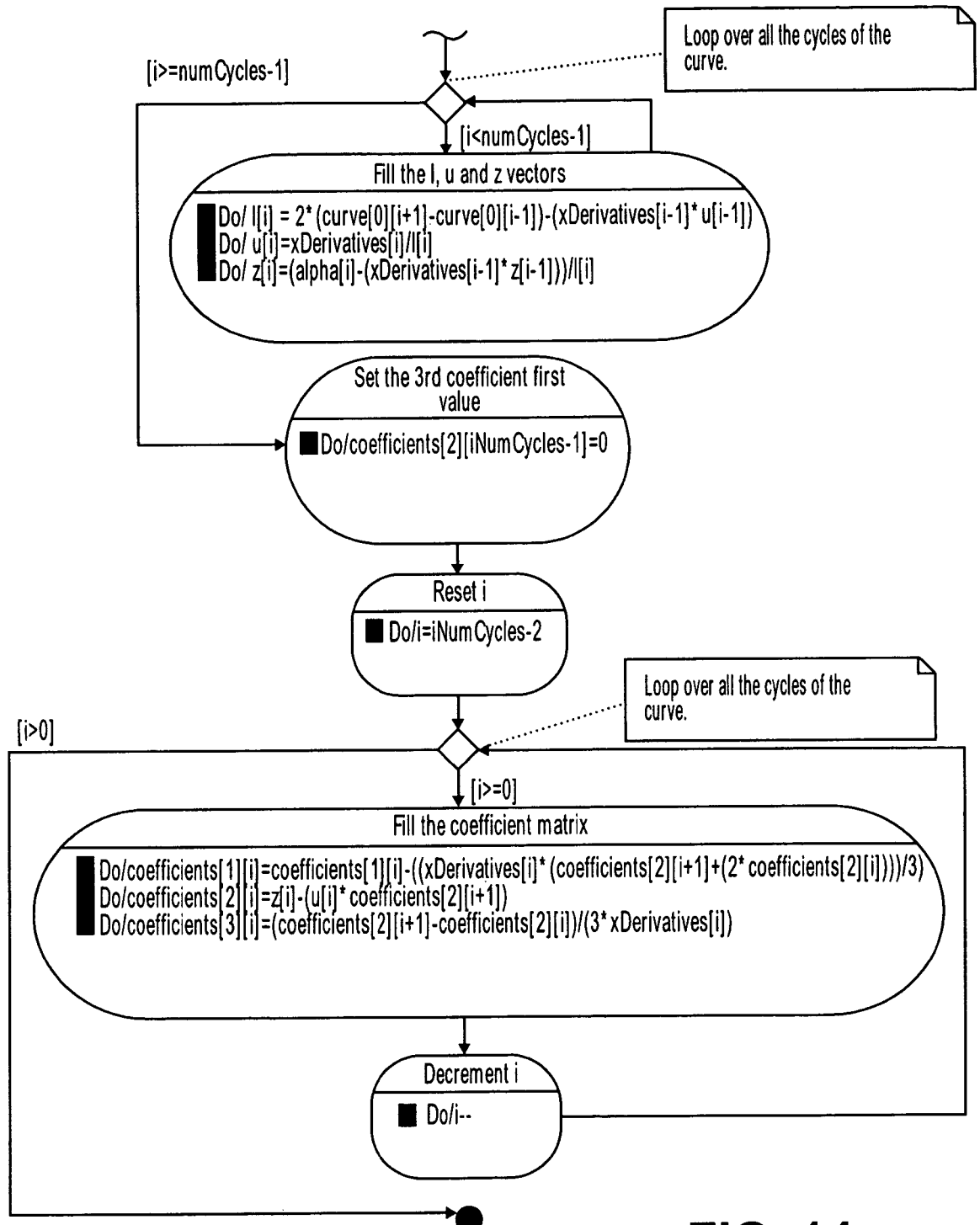

A cubic spline is a curve constructed of piecewise third-order polynomials which pass through a set of control points. In method of the present invention, the set of control points is the set of all the non-spiky data points (i.e., the data set with points identified as not satisfying the z-test threshold removed). FIG. 14 illustrates a flowchart of a cubic spline interpolation calculation process according to one embodiment of the present invention. Other spline interpolation processes may be used, such as first degree spline, second degree spline and trigonometric spline interpolation processes. In another aspect, other interpolation methods may be used, or the Levenberg-Marquardt regression process of the present invention, as applied to the sigmoid function and the data set with the spikes removed, may be used to determine interpolated values for the removed spike points. Other interpolation processes might include an Aitken interpolation algorithm, a Bessell interpolation algorithm, an Everett interpolation algorithm, a Gauss interpolation algorithm, a Hermite interpolation algorithm, a Lagrange interpolation algorithm, a Newton-Cotes interpolation algorithm, an Osculating interpolation algorithm, or a Thiele's interpolation algorithm.

As the Levenberg-Marquardt approximation in some cases may be slightly off, especially in the elbow region of a PCR curve or other growth curve, it is important to prevent the algorithm from shifting the curve. Therefore, in one aspect, spikes of width of 3 points or less are corrected; if more than 3 consecutive points have a Z-Value above the threshold, only the point that has the highest Z-Value of the consecutive points will be considered a spike. This aspect is shown in FIG. 16. It should be appreciated that a window of less than or greater than 3 may be used.

Figure 15:
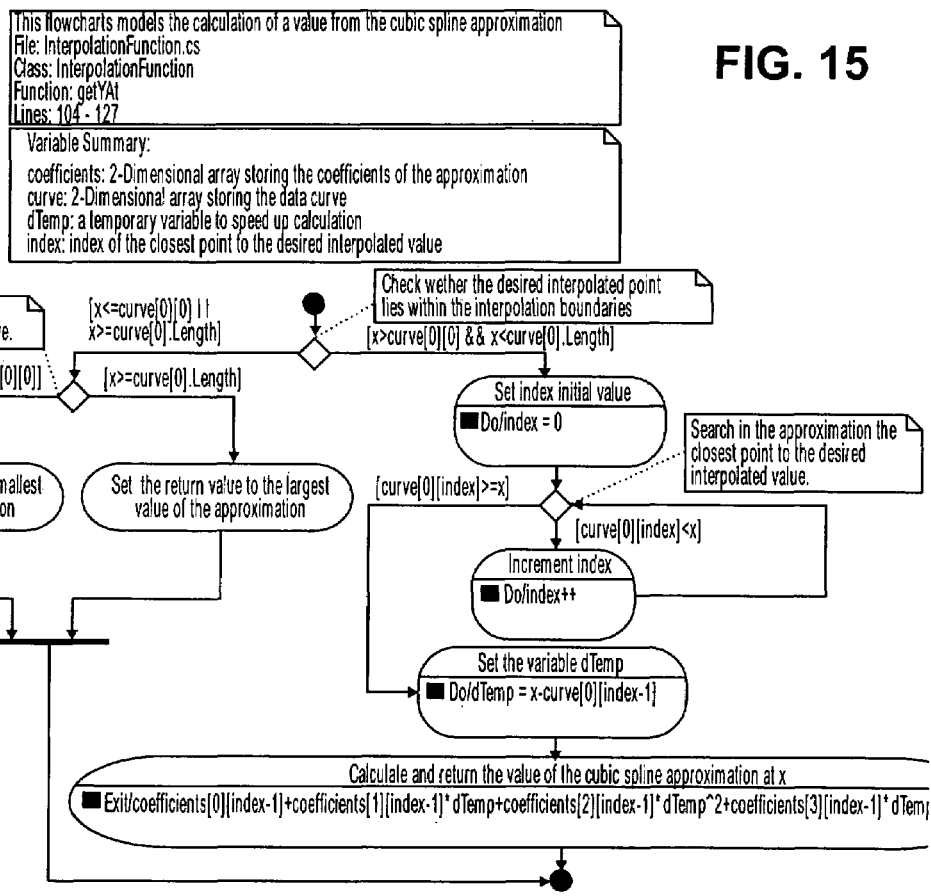
FIG. 15 illustrates an embodiment of a cubic spline interpolation method used to interpolate a replacement value for identified spike points.

Once a cubic spline approximation of the curve has been calculated, it can be used to interpolate the spike points. FIG. 15 illustrates an embodiment of a cubic spline interpolation method used to interpolate a replacement value for identified spike points. As shown, if the spike point lies within the cubic spline boundaries, then the following equation is used to calculate the value of the spike:

$$y_{interpolated} = a_{p1} + b_{p1}*(x_p - x_{p1}) + c_{p1}*(x_p - x_{p1})^2 + d_{p1}*(x_p - x_{p1})^3 \quad (12)$$

Where:
p is the spike point of which the interpolated value is sought,
p1 is the closest non-spiky point smaller than the spike point of which the interpolated value is sought,
$x_p$ is the x-value of p,
$x_{p1}$ is the x-value of p1,
$a_{p1}$, $b_{p1}$, $c_{p1}$ and $d_{p1}$ are the coefficients of the cubic spline at p1 previously calculated, and
$y_{initerpolated}$ is the interpolated value of the spike point.

If the spike point lies outside the boundaries of the cubic spline boundaries, i.e., if the point to be interpolated lies before or after the boundaries of the curve, then the smallest or largest value of the curve approximation is returned depending on whether the point lies before or after the curves boundaries, respectively.

Example

Figure 17B:
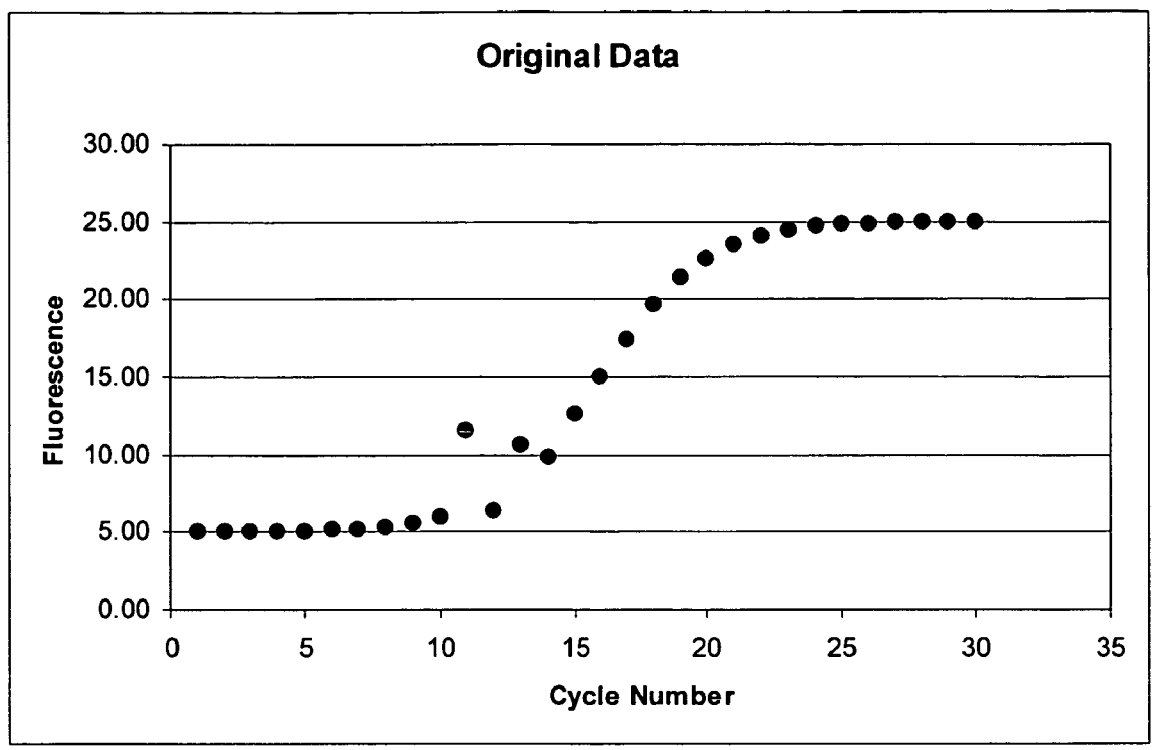
FIG. 17 shows (a) an example of a PCR growth curve data set, and (b) a plot of the original data set.
Figure 18B:
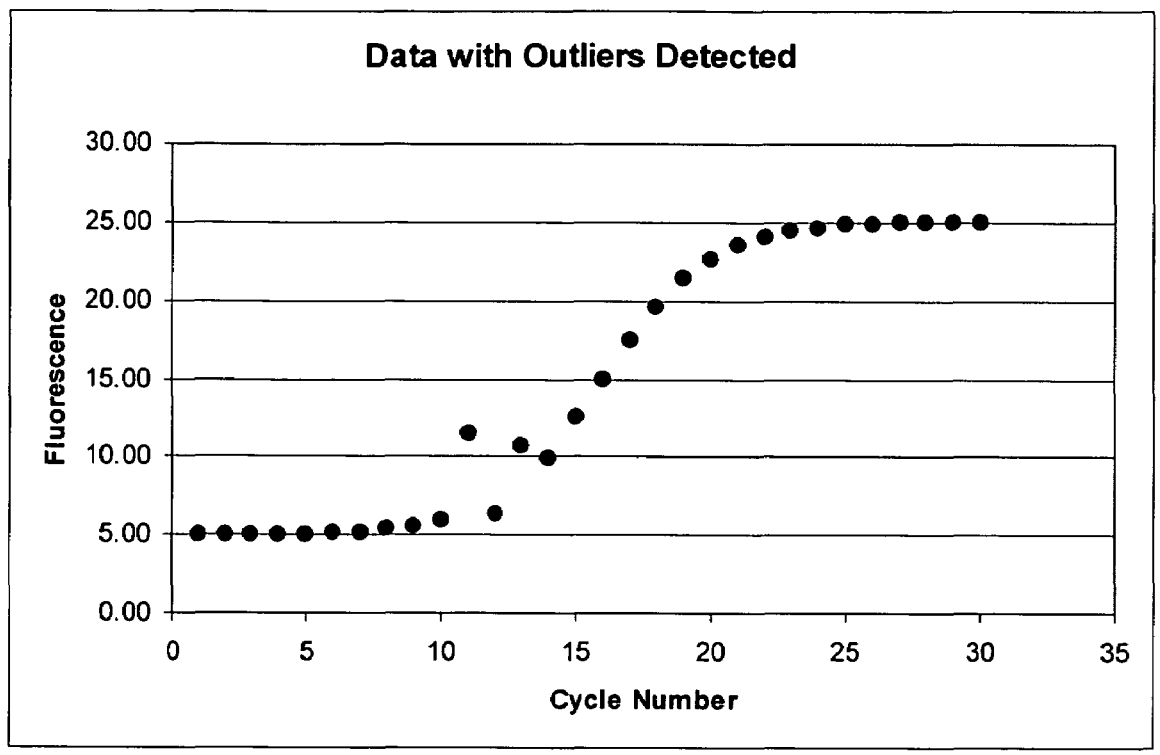
FIG. 18 shows (a) an example of the PCR growth curve data set of FIG. 17 with identified outliers removed, and (b) a plot of the data set with identified outliers removed.
Figure 19B:
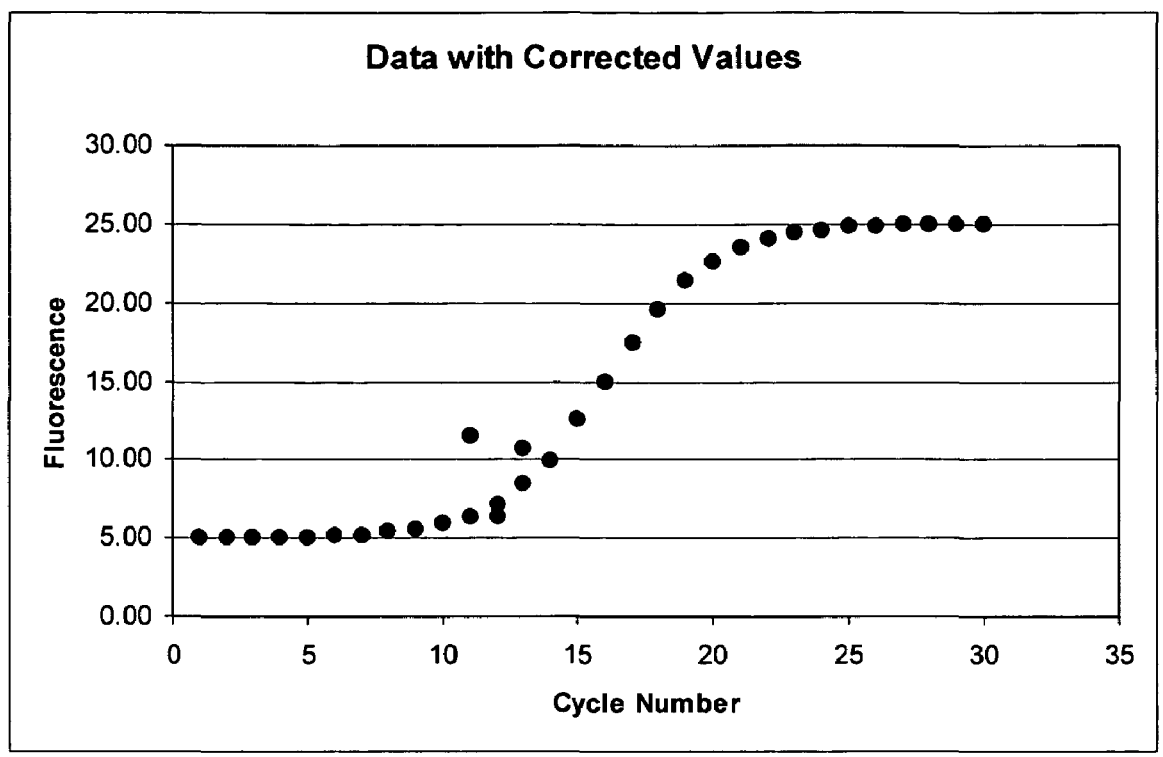
FIG. 19 shows (a) an example of the PCR growth curve data set of FIG. 17 with identified outliers replaced with interpolated values, and (b) a plot of the data set with identified outliers replaced with interpolated values.

FIGS. 17-19 illustrates aspects of the spike identification and removal process 100 of the present invention as applied to an example data set. FIG. 17a shows an example of a PCR growth curve data set, and FIG. 17b shows a plot of the original data set. FIG. 18a shows the PCR growth curve data set of FIG. 17 with identified outliers removed, and FIG. 18b shows a plot of the data set with identified outliers removed. FIG. 19a shows the PCR growth curve data set of FIG. 17 with identified outliers replaced with interpolated values, and FIG. 19b shows a plot of the data set with identified outliers replaced with interpolated values.

It should be appreciated that the spike identification and removal process 100, or portions thereof, may be implemented in computer code running on a processor of a computer system. The code includes instructions for controlling a processor to implement various aspects and steps of process 100. The code is typically stored on a hard disk, RAM or portable medium such as a CD, DVD, etc. Similarly, the process 100, or portions thereof, may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known. In certain aspects, the processes of the present invention can be coded using a variety of programming languages such as C, C++, C#, Fortran, VisualBasic, etc., as well as applications similar to Mathematica® which may provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A computer-implemented method of removing outlier spikes from a data set for a Polymerase Chain Reaction (PCR) growth curve, the method comprising the steps, implemented in a computer system having a processor, of:
receiving a data set for a PCR growth curve;
calculating an approximation of the curve by applying a Levenberg-Marquardt (LM) regression process to the data set and a double sigmoid function to determine parameters of the function;
determining whether one or more data points are outlier spikes by applying a statistical test to the approximation and the data set;
removing the data values for an identified spike from the data set to produce a modified data set; and
outputting the modified data set to a display device.

2. The method of claim 1, further comprising performing a goodness of fit test on said approximation to determine how well the data set and the approximation match.

3. The method of claim 2, wherein the goodness of fit test includes one of a Mean of Absolute Percentage Error (MAPE) test and a Median of Absolute Deviation (MAD) test.

4. The method of claim 3, wherein the goodness of fit test includes a MAPE test with a baseline adjustment.

5. The method of claim 1, wherein the statistical test includes a z-test.

6. The method of claim 1, wherein the LM regression process computes a distance between the approximation and the data set by minimizing a sum of absolute errors.

7. The method of claim 1, wherein the double sigmoid function is of the form:

$$a + bx + \frac{c}{(1 + \exp^{-d(x-e)})(1 + \exp^{-f(x-g)})},$$

and wherein calculating includes iteratively determining one or more of the parameters a, b, c, d, e, f and g of the function.

8. The method of claim 1, further comprising replacing the data values of the outlier spikes in the modified data set with data values determined by applying an interpolation algorithm to the modified data set.

9. The method of claim 8, wherein the interpolation algorithm is a spline interpolation algorithm.

10. The method of claim 9, wherein the spline interpolation algorithm is selected from the group consisting of a first degree spline interpolation algorithm, a second degree spline interpolation algorithm, a cubic spline interpolation algorithm and a trigonometric spline interpolation algorithm.

11. The method of claim 8, wherein applying an interpolation algorithm to the modified data set includes calculating an approximation of the curve by applying a Levenberg-Marquardt (LM) regression process to the modified data set and a double sigmoid function.

12. The method of claim 1, wherein performing the statistical test includes:
performing a first z-test on the data set using a first threshold value to identify a first set of zero or more spikes;
removing the data values for the first set of spikes from the data set to produce a modified data set; and
performing a second z-test on the modified data set using a second threshold value to identify a second set of zero or more spikes, wherein the first threshold value is greater than the second threshold value.

13. The method of claim 1, wherein said data set includes a plurality of first data points for a kinetic Polymerase Chain Reaction (PCR) process, each first data point having a pair of coordinate values (x,y), wherein x represents the cycle number and y represents an accumulation of amplified polynucleotide.

14. The method of claim 1, further comprising displaying the modified data set on a display.

15. The method of claim 8, further comprising displaying the modified data set and the replaced values on a display.

16. A Polymerase Chain Reaction (PCR) system, comprising:
a PCR data acquisition device that generates a PCR data set representing a PCR amplification curve; and
a processor adapted to receive and to process the PCR data set to identify and remove outlier spikes from the data set by:
calculating an approximation of the curve by applying a Levenberg-Marquardt (LM) regression process to the data set and a double sigmoid function to determine parameters of the function;
determining whether one or more data points are outlier spikes by applying a statistical test to the approximation and the data set;
removing the data values for an identified spike from the data set to produce a modified data set; and
outputting the modified data set to a display device.

17. The system of claim 16, wherein the double sigmoid function is of the form:

$$a + bx + \frac{c}{(1 + \exp^{-d(x-e)})(1 + \exp^{-f(x-g)})},$$

and wherein calculating includes iteratively determining one or more of the parameters a, b, c, d, e, f and g of the function.

18. A physical computer-readable medium that stores code for controlling a processor to identify and remove outlier spikes in a data set for a Polymerase Chain Reaction (PCR) amplification curve, the code including instructions to:
calculate an approximation of the curve by applying a Levenberg-Marquardt (LM) regression process to the data set and a double sigmoid function to determine parameters of the function;
determine whether one or more data points are outlier spikes by applying a statistical test to the approximation and the data set;
remove the data values for an identified spike from the data set to produce a modified data set; and
output the modified data set to a display device.

19. The computer-readable medium of claim 18, wherein the double sigmoid function is of the form:

$$a + bx + \frac{c}{(1 + \exp^{-d(x-e)})(1 + \exp^{-f(x-g)})},$$

and wherein the instructions to calculate includes include instructions to iteratively determine one or more of the parameters a, b, c, d, e, f and g of the function.

20. The computer-readable medium of claim 18, wherein the code further includes instructions to replace the data values of the outlier spikes in the modified data set with data values determined by applying an interpolation algorithm to the modified data set.

21. The computer readable medium of claim 18, wherein the physical medium comprises one of a CD, a DVD, a hard disk, or a RAM.

* * * * *